(12) United States Patent
Jeschke et al.

(10) Patent No.: US 8,324,130 B2
(45) Date of Patent: Dec. 4, 2012

(54) SYNERGISTIC ACTIVE INGREDIENT COMBINATIONS

(75) Inventors: Peter Jeschke, Gladbach (DE); Robert Velten, Langenfeld (DE); Thomas Schenke, Gladbach (DE); Wolfram Andersch, Gladbach (DE); Heike Hungenberg, Langenfeld (DE); Wolfgang Thielert, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 403 days.

(21) Appl. No.: 12/301,150

(22) PCT Filed: May 16, 2007

(86) PCT No.: PCT/EP2007/004375
§ 371 (c)(1),
(2), (4) Date: Mar. 3, 2009

(87) PCT Pub. No.: WO2007/134778
PCT Pub. Date: Nov. 29, 2007

(65) Prior Publication Data
US 2009/0280981 A1 Nov. 12, 2009

(30) Foreign Application Priority Data
May 18, 2006 (DE) .......................... 10 2006 023 263

(51) Int. Cl.
| | | |
|---|---|---|
| A01N 25/26 | (2006.01) | |
| A01N 43/40 | (2006.01) | |
| A01N 43/02 | (2006.01) | |
| A01N 43/00 | (2006.01) | |
| A01N 63/00 | (2006.01) | |
| A61K 31/44 | (2006.01) | |
| A61K 31/435 | (2006.01) | |

(52) U.S. Cl. ........ 504/100; 504/117; 504/130; 504/140; 514/183; 514/277; 514/336

(58) Field of Classification Search ................ 504/100, 504/117, 130, 140; 514/183, 277, 336
See application file for complete search history.

(56) References Cited

U.S. PATENT DOCUMENTS

| | | |
|---|---|---|
| 1,972,961 A | 9/1934 | Tisdale et al. |
| 2,504,404 A | 4/1950 | Flenner et al. |
| 2,553,770 A | 5/1951 | Kittleson |
| 2,588,428 A | 3/1952 | Stewart et al. |
| 3,010,968 A | 11/1961 | Loux |
| 3,178,447 A | 4/1965 | Kohn |
| 3,206,468 A | 9/1965 | Grenda |
| 3,248,400 A | 4/1966 | Flieg |
| 3,249,499 A | 5/1966 | Von Schmeling et al. |
| 3,285,929 A | 11/1966 | Klauke et al. |
| 3,290,353 A | 12/1966 | Battershel et al. |
| 3,499,951 A | 3/1970 | Schrader et al. |
| 3,513,241 A | 5/1970 | Hoyer et al. |
| 3,546,813 A | 12/1970 | Frohberger et al. |
| 3,629,428 A | 12/1971 | Seki et al. |
| 3,631,176 A | 12/1971 | Klopping |
| 3,745,170 A | 7/1973 | Fujinami |
| 3,745,187 A | 7/1973 | Noguchi et al. |
| 3,755,350 A | 8/1973 | Sauli |
| 3,856,814 A | 12/1974 | Taninaka et al. |
| 3,912,752 A | 10/1975 | Meiser et al. |
| 3,952,002 A | 4/1976 | Kramer et al. |
| 3,966,750 A | 6/1976 | Mangold et al. |
| 3,991,071 A | 11/1976 | Brookes et al. |
| 4,046,911 A | 9/1977 | Hubele |
| 4,068,077 A | 1/1978 | Goetz et al. |
| 4,079,062 A | 3/1978 | Van Reet et al. |
| 4,093,743 A | 6/1978 | Yabutani et al. |
| 4,127,673 A | 11/1978 | Yamada et al. |
| 4,139,616 A | 2/1979 | Ducret et al. |
| 4,151,299 A | 4/1979 | Hubele |
| 4,239,760 A | 12/1980 | Sasse et al. |
| 4,291,049 A | 9/1981 | Bosone et al. |
| 4,331,670 A | 5/1982 | Nishiyama et al. |
| 4,341,782 A | 7/1982 | Konishi et al. |
| 4,432,989 A | 2/1984 | Spencer |
| 4,496,551 A | 1/1985 | Moberg |

(Continued)

FOREIGN PATENT DOCUMENTS

CA   1022458   12/1977

(Continued)

OTHER PUBLICATIONS

International Search Report for PCT/EP2007/004375 dated Sep. 30, 2008 (6 pages).
Fungicide Manual, 1991, pp. 249 and 827.
Williams, Alec, "Antifouling Marine Coatings," Noyes Data Coporation, 1973, pp. 1-249.
Colby, S.R., "Calculating Synergistic and Atagonistic Responses of Herbicide Combinations," Weeds, 1967, pp. 20-22.

(Continued)

*Primary Examiner* — Richard Schnizer
*Assistant Examiner* — Jane C Oswecki
(74) *Attorney, Agent, or Firm* — Baker Donelson Bearman, Caldwell & Berkowitz, PC

(57) ABSTRACT

The novel active compound combinations comprising compounds of the formula (I)

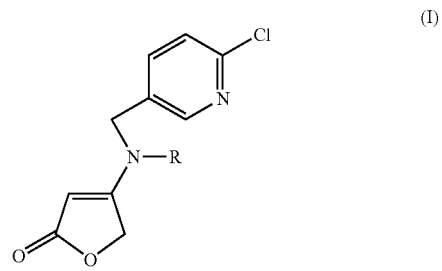

where
R represents methyl or cyclopropyl,
and at least one compound selected from the active compound groups (1) to (24) listed in the description have very good insecticidal and fungicidal properties.

22 Claims, No Drawings

U.S. PATENT DOCUMENTS

| | | | |
|---|---|---|---|
| 4,532,341 A | 7/1985 | Holmwood et al. |
| 4,551,469 A | 11/1985 | Parry et al. |
| 4,598,085 A | 7/1986 | Heeres et al. |
| 4,608,385 A | 8/1986 | Noguchi et al. |
| 4,652,580 A | 3/1987 | Janssen et al. |
| 4,659,739 A | 4/1987 | Yoshioka et al. |
| 4,664,696 A | 5/1987 | Schaub |
| 4,705,800 A | 11/1987 | Nyfeler et al. |
| 4,731,106 A | 3/1988 | Green et al. |
| 4,829,085 A | 5/1989 | Wenderoth et al. |
| 4,840,959 A | 6/1989 | Oda et al. |
| 4,851,405 A | 7/1989 | Kramer et al. |
| 4,877,441 A | 10/1989 | Mori et al. |
| 4,902,705 A | 2/1990 | Hirota et al. |
| 4,910,200 A | 3/1990 | Curtze et al. |
| 4,920,139 A | 4/1990 | Fujimoto |
| 4,931,560 A | 6/1990 | Hubele |
| 4,931,581 A | 6/1990 | Schurter et al. |
| 4,957,933 A | 9/1990 | Geffken et al. |
| 4,988,734 A | 1/1991 | Kraatz et al. |
| 4,992,438 A | 2/1991 | Ito et al. |
| 4,995,898 A | 2/1991 | Nasu et al. |
| 5,021,581 A | 6/1991 | Clough et al. |
| 5,059,623 A | 10/1991 | Kruger et al. |
| 5,081,141 A | 1/1992 | Colle et al. |
| 5,087,635 A | 2/1992 | Shaber |
| 5,112,849 A | 5/1992 | Staub et al. |
| 5,145,856 A | 9/1992 | Clough et al. |
| 5,185,342 A | 2/1993 | Hayase et al. |
| 5,221,691 A | 6/1993 | Clough et al. |
| 5,254,584 A | 10/1993 | Michelotti et al. |
| 5,256,683 A | 10/1993 | Hutt et al. |
| 5,266,585 A | 11/1993 | Hubele et al. |
| 5,304,572 A | 4/1994 | Michelotti et al. |
| 5,306,712 A | 4/1994 | Tobitsuka et al. |
| 5,334,607 A | 8/1994 | Sauter et al. |
| 5,407,902 A | 4/1995 | Oda et al. |
| 5,453,531 A | 9/1995 | Seitz et al. |
| 5,486,621 A | 1/1996 | Phillion et al. |
| 5,514,643 A | 5/1996 | Rew et al. |
| 5,593,996 A | 1/1997 | Pees et al. |
| 5,679,676 A | 10/1997 | Kruger et al. |
| 5,723,491 A | 3/1998 | Nuninger et al. |
| 5,747,497 A | 5/1998 | Bereznak et al. |
| 5,747,518 A | 5/1998 | Yoshikawa et al. |
| 5,789,428 A | 8/1998 | Shibata et al. |
| 5,789,430 A | 8/1998 | Jautelat et al. |
| 5,869,517 A | 2/1999 | Muller et al. |
| 5,922,905 A | 7/1999 | Curtze et al. |
| 5,948,932 A | 9/1999 | Grote et al. |
| 5,986,135 A | 11/1999 | Pfrengle et al. |
| 5,998,450 A | 12/1999 | Eicken et al. |
| 6,056,554 A | 5/2000 | Samole |
| 6,103,717 A | 8/2000 | Heinemann et al. |
| 6,277,858 B1 | 8/2001 | Walter |
| 6,355,634 B1 | 3/2002 | Isenring et al. |
| 6,616,054 B1 | 9/2003 | Norton |
| 6,683,211 B1 | 1/2004 | Lamberth et al. |
| 2001/0018442 A1 | 8/2001 | Gayer et al. |
| 2002/0198222 A1 | 12/2002 | Bruns et al. |
| 2003/0027842 A1 | 2/2003 | Assmann et al. |
| 2003/0093133 A1 | 5/2003 | Crowe et al. |
| 2003/0171410 A1 | 9/2003 | Moloney et al. |
| 2004/0039043 A1 | 2/2004 | Elbe et al. |
| 2004/0110771 A1 | 6/2004 | Blasco et al. |
| 2004/0192672 A1 | 9/2004 | Wegmann et al. |
| 2004/0204470 A1 | 10/2004 | Elbe et al. |
| 2005/0119130 A1 | 6/2005 | Walter |
| 2005/0124815 A1 | 6/2005 | Elbe et al. |
| 2005/0143428 A1 | 6/2005 | Dunkel et al. |
| 2006/0116414 A1 | 6/2006 | Dunkel et al. |
| 2006/0211771 A1 | 9/2006 | Elbe et al. |
| 2007/0060579 A1 | 3/2007 | Wachendorff-Neumann et al. |
| 2007/0298966 A1 * | 12/2007 | Fischer et al. ............ 504/103 |
| 2008/0280953 A1 | 11/2008 | Gorgens et al. |
| 2009/0018015 A1 | 1/2009 | Wachendorff-Neumann et al. |

FOREIGN PATENT DOCUMENTS

| | | |
|---|---|---|
| CA | 1040530 | 10/1978 |
| CA | 1049547 | 2/1979 |
| CA | 1086734 | 9/1980 |
| DE | 140041 | 3/1902 |
| DE | 151404 | 5/1904 |
| DE | 1 081 446 B1 | 5/1960 |
| DE | 30 30 026 A1 | 3/1981 |
| EP | 0258161 A2 | 2/1988 |
| EP | 0262393 A1 | 6/1988 |
| EP | 0329397 A1 | 8/1989 |
| EP | 0539588 | 5/1993 |
| EP | 0539588 A1 | 5/1993 |
| EP | 0860438 A1 | 8/1998 |
| GB | 935981 A | 4/1963 |
| GB | 988630 A | 7/1965 |
| GB | 1094567 A | 12/1967 |
| GB | 1114155 A | 5/1968 |
| GB | 1103989 A | 12/1968 |
| WO | 98/23155 A1 | 6/1998 |
| WO | 2004080181 | 9/2004 |
| WO | WO 2006037475 A1 * | 4/2006 |
| WO | WO 2006040016 A1 * | 4/2006 |

OTHER PUBLICATIONS

Ungerer, "Marine paints—a speciality of the coastal coatings industry," Chem. Ind. XXXVII, Oct. 1985, pp. 730-732 (english translation).

* cited by examiner

SYNERGISTIC ACTIVE INGREDIENT COMBINATIONS

CROSS REFERENCE TO RELATED APPLICATIONS

This application is a §371 National Stage Application of PCT/EP2007/004375 filed May 16, 2007 which claims priority to German Application 10 2006 023 263.9 filed May 18, 2006.

BACKGROUND OF THE INVENTION

1. Field of the Invention

The present invention relates to novel active compound combinations comprising firstly a known compound of the formula (I) and secondly at least one known fungicidally active compound, which novel active compound combinations are highly suitable for controlling unwanted animal pests such as insects and unwanted phytopathogenic fungi.

2. Description of Related Art

It is already known that compounds of the formula (I) have insecticidal action (cf. EP 0 539 588 A1).

Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th Edition (1991), pages 249 and 827, EP-A 0 382 375, EP-A 0 515 901, DE-B2 2732257). However, the action of these compounds is likewise not always sufficient at low application rates.

Furthermore, it is already known that 1-(3,5-dimethyl-isoxazole-4-sulphonyl)-2-chloro-6,6-difluoro-[1,3]-di-oxolo-[4,5f]-benzimidazole has fungicidal properties (cf. WO 97/06171).

Finally, it is also known that substituted halopyrimidines have fungicidal properties (cf. DE-A1-196 46 407, EP-B-712 396).

SUMMARY OF THE INVENTION

We have now found novel active compound combinations having very good insecticidal and fungicidal properties and comprising at least one compound of the formula (I) (Group 1)

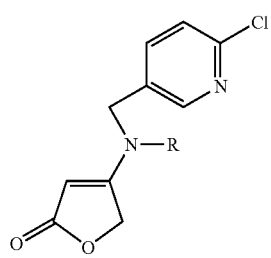

(I)

where
R represents methyl or cyclopropyl,
and at least one active compound selected from Groups (2) to (24) below:
Group (2) Strobilurins of the General Formula (II)

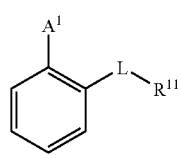

(II)

in which
$A^1$ represents one of the groups

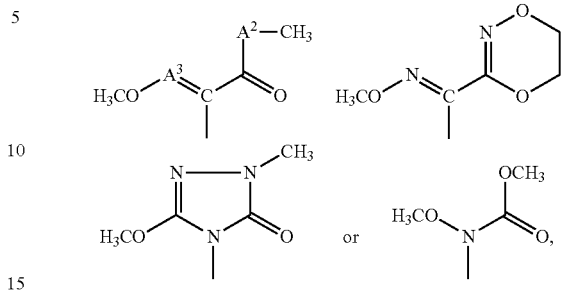

$A^2$ represents NH or O,
$A^3$ represents N or CH,
L represents one of the groups

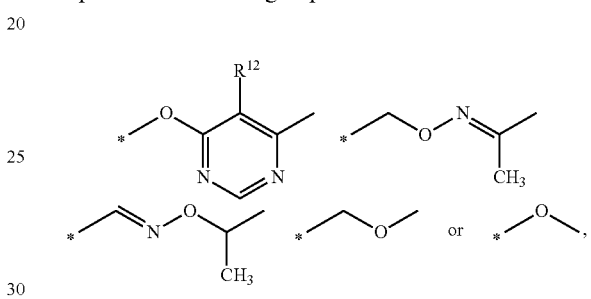

where the bond marked with an asterisk (*) is attached to the phenyl ring,
$R^{11}$ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)pyrazol-3-yl or represents 1,2-propanedione-bis(O-methyloxime)-1-yl,
$R^{12}$ represents hydrogen or fluorine;
Group (3) Triazoles of the General Formula (III)

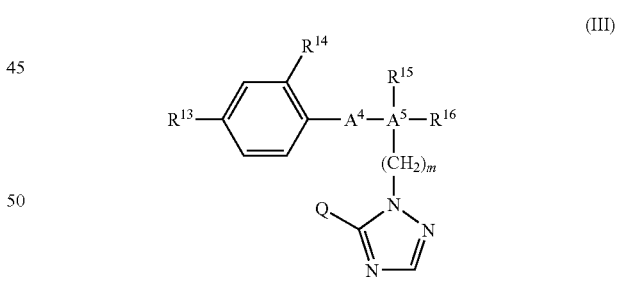

(III)

in which
Q represents hydrogen or SH,
m represents 0 or 1,
$R^{13}$ represents hydrogen, fluorine, chlorine, phenyl or 4-chlorophenoxy,
$R^{14}$ represents hydrogen or chlorine,
$A^4$ represents a direct bond, —$CH_2$—, —$(CH_2)_2$—, —O—, represents *—$CH_2$—$CHR^{17}$— or *—CH=$CR^{17}$—, where the bond marked with * is attached to the phenyl ring, in which case
$R^{15}$ and $R^{17}$ together represent —$CH_2$—$CH_2$—CH[CH($CH_3$)$_2$]— or —$CH_2$—$CH_2$—C($CH_3$)$_2$—,
$A^5$ represents C or Si (silicon), $A^4$ further represents —N($R^{17}$)— and $A^5$ furthermore together with $R^{15}$ and $R^{16}$ represents the group C=N—$R^{18}$, in which case $R^{17}$ and $R^{18}$ together represent the group

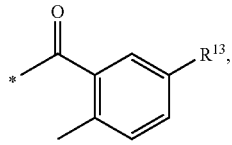

where the bond marked with * is attached to $R^{17}$, $R^{15}$ represents hydrogen, hydroxyl or cyano, $R^{16}$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl or phenyl, $R^{15}$ and $R^{16}$ furthermore together represent —O—$CH_2$—CH($R^{18}$)—O—, —O—$CH_2$—CH($R^{18}$)—$CH_2$—, or —O—CH-(2-chlorophenyl)-, $R^{18}$ represents hydrogen, $C_1$-$C_4$-alkyl or bromine;

Group (4) Sulphenamides of the General Formula (IV)

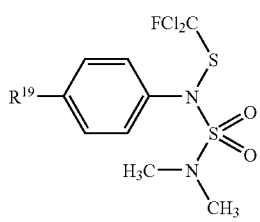

in which $R^{19}$ represents hydrogen or methyl;

Group (5) Valinamides Selected from
(5-1) iprovalicarb
(5-2) $N^1$-[2-(4-{[3-(4-chlorophenyl)-2-propynyl]oxy}-3-methoxyphenyl)ethyl]-$N^2$-(methylsulphonyl)-D-valinamide
(5-3) benthiavalicarb Group (6) Carboxamides of the General Formula (V)

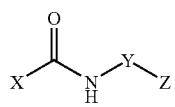

in which

X represents 2-chloro-3-pyridinyl, represents 1-methylpyrazol-4-yl which is substituted in the 3-position by methyl or trifluoromethyl and in the 5-position by hydrogen or chlorine, represents 4-ethyl-2-ethylamino-1,3-thiazol-5-yl, represents 1-methylcyclohexyl, represents 2,2-dichloro-1-ethyl-3-methylcyclopropyl, represents 2-fluoro-2-propyl, 3,4-dichloroisothiazol-5-yl, 5,6-dihydro-2-methyl-1,4-oxathiin-3-yl, 4-methyl-1,2,3-thiadiazol-5-yl, 4,5-dimethyl-2-trimethylsilylthiophen-3-yl, 1-methylpyrrol-3-yl which is substituted in the 4-position by methyl or trifluoromethyl and in the 5-position by hydrogen or chlorine, or represents phenyl which is mono- to trisubstituted by identical or different substituents from the group consisting of chlorine, methyl and trifluoromethyl, Y represents a direct bond, $C_1$-$C_6$-alkanediyl (alkylene) which is optionally substituted by chlorine, cyano or oxo, represents $C_2$-$C_6$-alkenediyl (alkenylene) or thiophenediyl, Z represents hydrogen, $C_1$-$C_6$-alkyl or the group

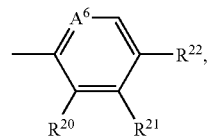

in which $A^6$ represents CH or N, $R^{20}$ represents hydrogen, chlorine, cyano, $C_1$-$C_6$-alkyl, phenyl which is optionally mono- or disubstituted by identical or different substituents from the group consisting of chlorine and di($C_1$-$C_3$-alkyl)aminocarbonyl, $R^{21}$ represents hydrogen, chlorine or isopropoxy, $R^{22}$ represents hydrogen, chlorine, hydroxyl, methyl, trifluoromethyl or di($C_1$-$C_3$-alkyl)aminocarbonyl, $R^{20}$ and $R^{21}$ furthermore together represent *—CH($CH_3$)—$CH_2$—C($CH_3$)$_2$— or *—CH($CH_3$)—O—C($CH_3$)$_2$— where the bond marked with * is attached to $R^{20}$;

Group (7) Dithiocarbamates Selected from
(7-1) mancozeb
(7-2) maneb
(7-3) metiram
(7-4) propineb
(7-5) thiram
(7-6) zineb
(7-7) ziram Group (8) Acylalanines of the General Formula (VI)

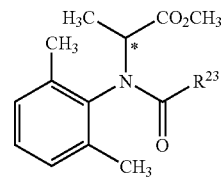

in which
* marks a carbon atom in the R or the S configuration, preferably in the S configuration,
$R^{23}$ represents benzyl, furyl or methoxymethyl;

Group (9): Anilinopyrimidines of the General Formula (VII)

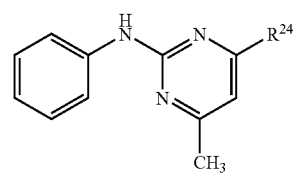

in which
$R^{24}$ represents methyl, cyclopropyl or 1-propynyl;

Group (10): Benzimidazoles of the General Formula (VIII)

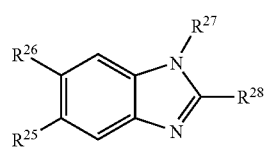

in which
$R^{25}$ and $R^{26}$ each represent hydrogen or together represent —O—CF$_2$—O—,
$R^{27}$ represents hydrogen, $C_1$-$C_4$-alkylaminocarbonyl or represents 3,5-dimethylisoxazol-4-ylsulphonyl,
$R^{28}$ represents chlorine, methoxycarbonylamino, chlorophenyl, furyl or thiazolyl;
Group (11): Carbamates of the General Formula (IX)

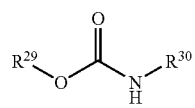
(IX)

in which
$R^{29}$ represents n- or isopropyl,
$R^{30}$ represents di($C_1$-$C_2$-alkyl)amino-$C_2$-$C_4$-alkyl or diethoxyphenyl,
salts of these compounds also being included;
Group (12): Dicarboximides Selected from
(12-1) captafol
(12-2) captan
(12-3) folpet
(12-4) iprodione
(12-5) procymidone
(12-6) vinclozolin
Group (13): Guanidines Selected from
(13-1) dodine
(13-2) guazatine
(13-3) iminoctadine triacetate
(13-4) iminoctadine tris(albesilate)
Group (14): Imidazoles Selected from
(14-1) cyazofamid
(14-2) prochloraz
(14-3) triazoxide
(14-4) pefurazoate
Group (15): Morpholines of the General Formula (X)

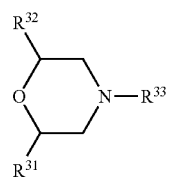
(X)

in which
$R^{31}$ and $R^{32}$ independently of one another represent hydrogen or methyl,
$R^{33}$ represents $C_1$-$C_{14}$-alkyl (preferably $C_{12}$-$C_{14}$-alkyl), $C_5$-$C_{12}$-cycloalkyl (preferably $C_{10}$-$C_{12}$-cycloalkyl), phenyl-$C_1$-$C_4$-alkyl, which may be substituted in the phenyl moiety by halogen or $C_1$-$C_4$-alkyl or represents acrylyl which is substituted by chlorophenyl and dimethoxyphenyl;
Group (16): Pyrroles of the General Formula (XI)

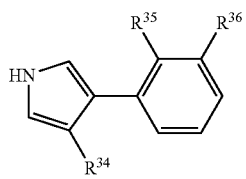
(XI)

in which
$R^{34}$ represents chlorine or cyano,
$R^{35}$ represents chlorine or nitro,
$R^{36}$ represents chlorine,
$R^{35}$ and $R^{36}$ furthermore together represent —O—CF$_2$—O—;
Group (17): (Thio)phosphonates Selected from
(17-1) fosetyl-Al,
(17-2) phosphonic acid,
(17-3) tolclophos-methyl;
Group (18): Phenylethanamides of the General Formula (XII)

(XII)

in which
$R^{37}$ represents unsubstituted or fluorine-, chlorine-, bromine-, methyl- or ethyl-substituted phenyl, 2-naphthyl, 1,2,3,4-tetrahydronaphthyl or indanyl;
Group (19): Fungicides Selected from
(19-1) acibenzolar-5-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-14) 2,3-dibutyl-6-chlorothieno[2,3-d]pyrimidin-4(3H)-one
(19-15) probenazole
(19-16) isoprothiolane
(19-17) kasugamycin
(19-18) phthalide
(19-19) ferimzone
(19-20) tricyclazole
(19-21) cyprosulfamide
(19-22) mandipropamid
(19-23) quinoxyfen (known from EP-A 326 330) of the formula

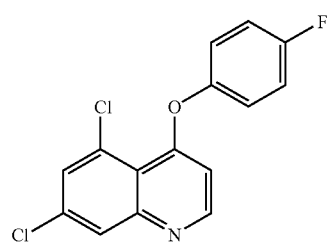

(19-24) proquinazid (known from WO 94/26722) of the formula

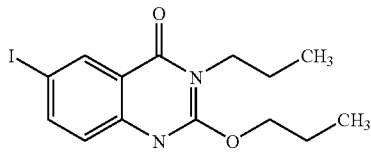

Group (20): (Thio)urea Derivatives Selected from
(20-1) pencycuron
(20-2) thiophanate-methyl
(20-3) thiophanate-ethyl
Group (21): Amides of the General Formula (XIII)

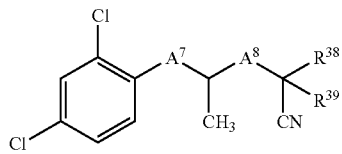

(XIII)

in which
$A^7$ represents a direct bond or —O—,
$A^8$ represents —C(=O)NH— or —NHC(=O)—,
$R^{38}$ represents hydrogen or $C_1$-$C_4$-alkyl,
$R^{39}$ represents $C_1$-$C_6$-alkyl;
Group (22): Triazolopyrimidines of the General Formula (XIV)

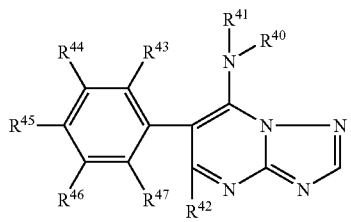

(XIV)

in which
$R^{40}$ represents $C_1$-$C_6$-alkyl or $C_2$-$C_6$-alkenyl,
$R^{41}$ represents $C_1$-$C_6$-alkyl,
$R^{40}$ and $R^{41}$ furthermore together represent $C_4$-$C_5$-alkanediyl (alkylene) which is mono- or disubstituted by $C_1$-$C_6$-alkyl,
$R^{42}$ represents bromine or chlorine,
$R^{43}$ and $R^{47}$ independently of one another represent hydrogen, fluorine, chlorine or methyl,
$R^{44}$ and $R^{46}$ independently of one another represent hydrogen or fluorine,
$R^{45}$ represents hydrogen, fluorine or methyl,
Group (23): Iodochromones of the General Formula (XV)

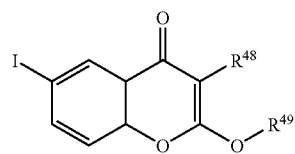

(XV)

in which
$R^{48}$ represents $C_1$-$C_6$-alkyl,
$R^{49}$ represents $C_1$-$C_6$-alkyl, $C_2$-$C_6$-alkenyl or $C_2$-$C_6$-alkynyl;
Group (24): Biphenylcarboxamides of the General Formula (XVI)

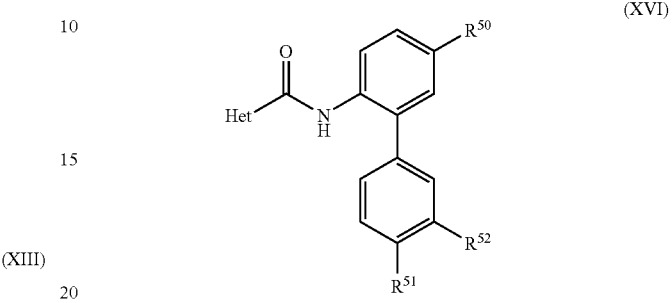

(XVI)

in which
$R^{50}$ represents hydrogen or fluorine,
$R^{51}$ represents fluorine, chlorine, bromine, methyl, trifluoromethyl, trifluoromethoxy, —CH=N—OMe or —C(Me)=N—OMe,
$R^{52}$ represents hydrogen, fluorine, chlorine, bromine, methyl or trifluoromethyl,
Het represents one of the radicals Het1 to Het7 below:

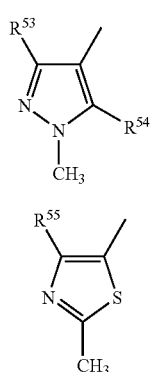

Het1

Het2

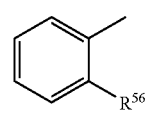

Het3

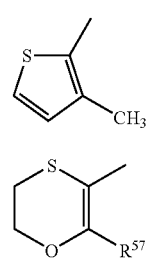

Het4

Het5

Het6

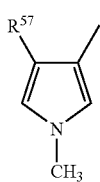

Het7

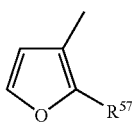

$R^{53}$ represents iodine, methyl, difluoromethyl or trifluoromethyl, $R^{54}$ represents hydrogen, fluorine, chlorine or methyl, $R^{55}$ represents methyl, difluoromethyl or trifluoromethyl, $R^{56}$ represents chlorine, bromine, iodine, methyl, difluoromethyl or trifluoromethyl, $R^{57}$ represents methyl or trifluoromethyl.

Surprisingly, the fungicidal action of the active compound combinations according to the invention is considerably better than the sum of the activities of the individual active compounds. Thus, an unforeseeable true synergistic effect is present, and not just an addition of actions.

Surprisingly, the insecticidal action of the active compound combinations according to the invention is considerably better than the sum of the activities of the individual active compounds. Thus, an unforeseeable true synergistic effect is present, and not just an addition of actions.

The formula (I) embraces the following preferred mixing partners:

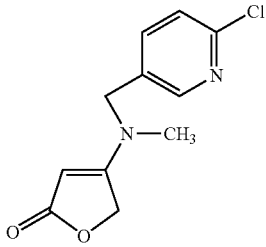

(Ia): 4-[[(6-chloropyridin-3-yl)methyl](methylamino)]furan-2-(5H)-one

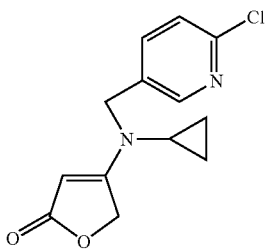

(Ib): 4-[[(6-chloropyridin-3-yl)methyl] (cyclopropylamino)]furan-2-(5H)-one

Emphasis is given to active compound combinations according to the invention which, in addition to the compound of the formula (Ia), comprise one or more, preferably one, active compound of Groups (2) to (24).

Emphasis is given to active compound combinations according to the invention which, in addition to the compound of the formula (Ib), comprise one or more, preferably one, active compound of Groups (2) to (24).

DETAILED DESCRIPTION OF A PREFERRED EMBODIMENT

The formula (II) embraces the following preferred mixing partners of group (2):

(2-1) azoxystrobin (known from EP-A 0 382 375) of the formula

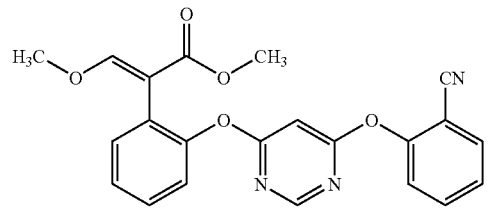

(2-2) fluoxastrobin (known from DE-A 196 02 095) of the formula

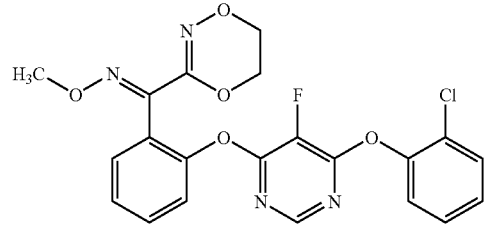

(2-3) (2E)-2-(2-{[6-(3-chloro-2-methylphenoxy)-5-fluoro-4-pyrimidinyl]oxy}phenyl)-2-(methoxyimino)-N-methylethanamide (known from DE-A 196 46 407, EP-B 0 712 396) of the formula

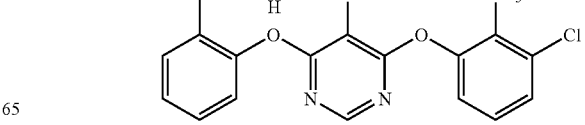

(2-4) trifloxystrobin (known from EP-A 0 460 575) of the formula

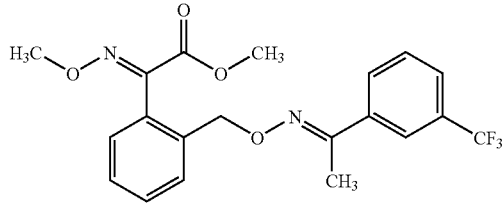

(2-5) (2E)-2-(methoxyimino)-N-methyl-2-(2-{[({(1E)-1-[3-(trifluoromethyl)phenyl]ethylidene}-amino)oxy]methyl}phenyl)ethanamide (known from EP-A 0 569 384) of the formula

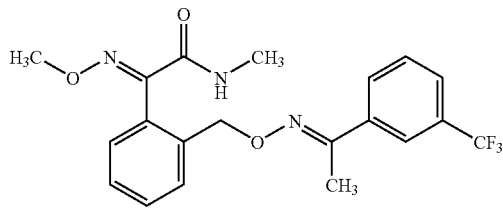

(2-6) (2E)-2-(methoxyimino)-N-methyl-2-{2-[(E)-({1-[3-(trifluoromethyl)phenyl)ethoxy}imino)methyl]phenyl}ethanamide (known from EP-A 0 596 254) of the formula

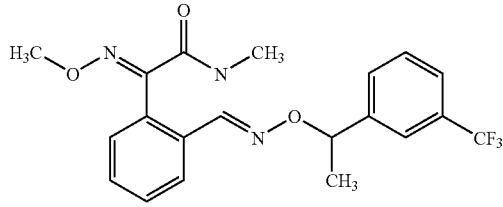

(2-7) orysastrobin (known from DE-A 195 39 324) of the formula

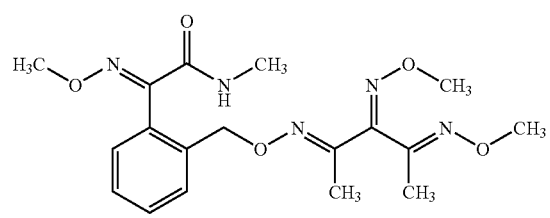

(2-8) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one (known from WO 98/23155) of the formula

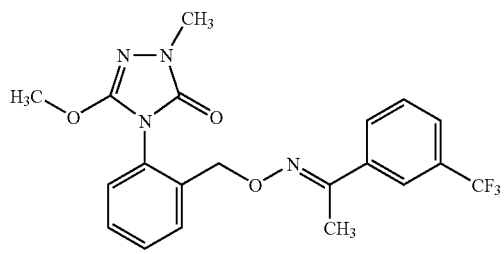

(2-9) kresoxim-methyl (known from EP-A 0 253 213) of the formula

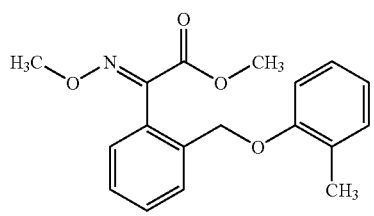

(2-10) dimoxystrobin (known from EP-A 0 398 692) of the formula

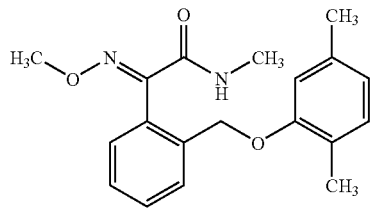

(2-11) picoxystrobin (known from EP-A 0 278 595) of the formula

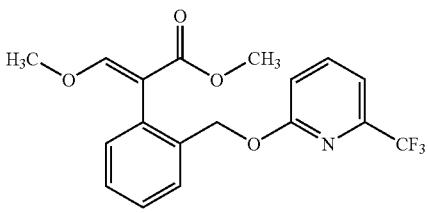

(2-12) pyraclostrobin (known from DE-A 44 23 612) of the formula

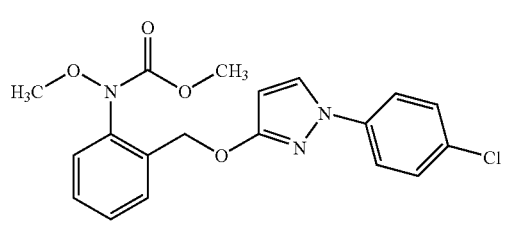

(2-13) metominostrobin (known from EP-A 0 398 692) of the formula

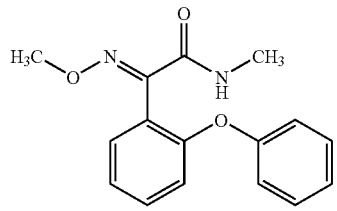

The formula (III) embraces the following preferred mixing partners of group (3):
(3-1) azaconazole (known from DE-A 25 51 560) of the formula

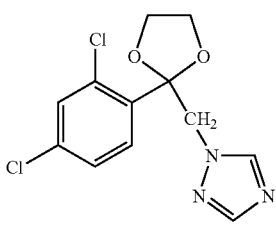

(3-2) etaconazole (known from DE-A 25 51 560) of the formula

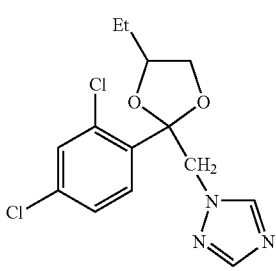

(3-3) propiconazole (known from DE-A 25 51 560) of the formula

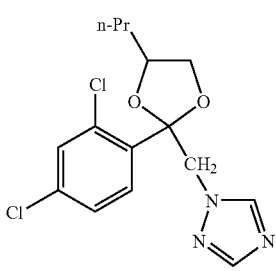

(3-4) difenoconazole (known from EP-A 0 112 284) of the formula

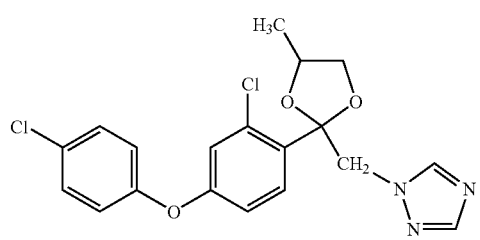

(3-5) bromuconazole (known from EP-A 0 258 161) of the formula

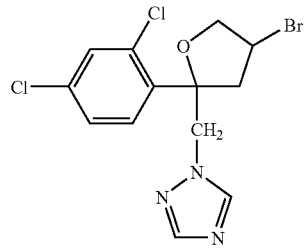

(3-6) cyproconazole (known from DE-A 34 06 993) of the formula

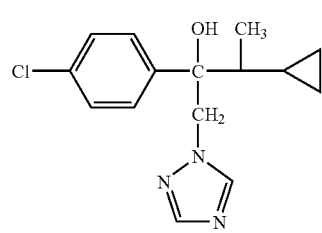

(3-7) hexaconazole (known from DE-A 30 42 303) of the formula

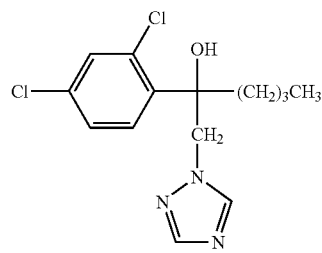

(3-8) penconazole (known from DE-A 27 35 872) of the formula

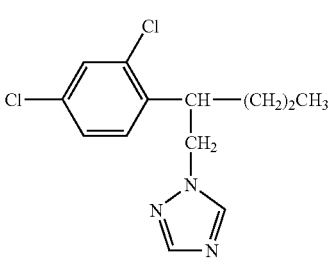

(3-9) myclobutanil (known from EP-A 0 145 294) of the formula

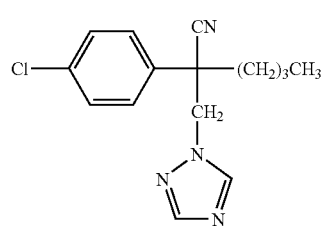

(3-10) tetraconazole (known from EP-A 0 234 242) of the formula

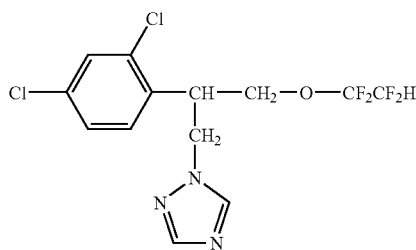

(3-11) flutriafol (known from EP-A 0 015 756) of the formula

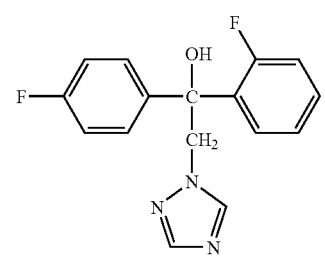

(3-12) epoxiconazole (known from EP-A 0 196 038) of the formula

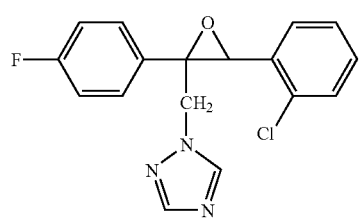

(3-13) flusilazole (known from EP-A 0 068 813) of the formula

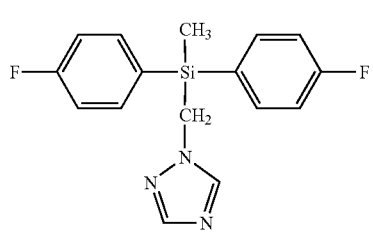

(3-14) simeconazole (known from EP-A 0 537 957) of the formula

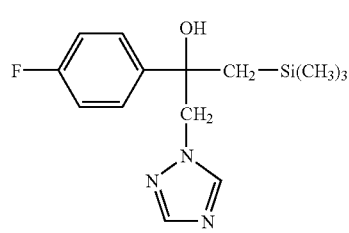

(3-15) prothioconazole (known from WO 96/16048) of the formula

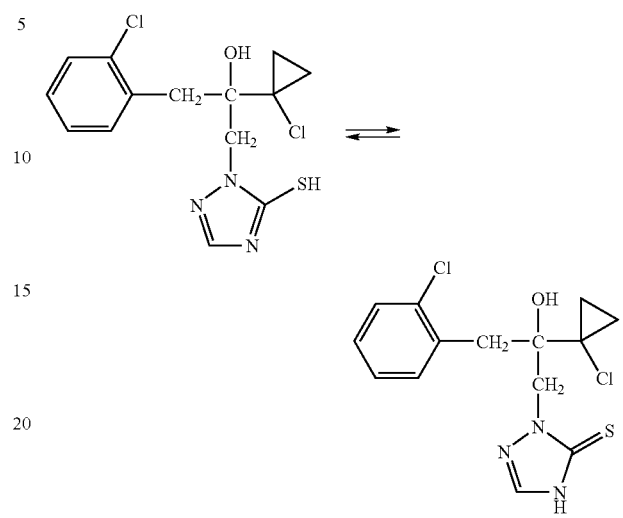

(3-16) fenbuconazole (known from DE-A 37 21 786) of the formula

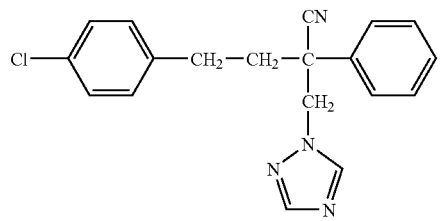

(3-17) tebuconazole (known from EP-A 0 040 345) of the formula

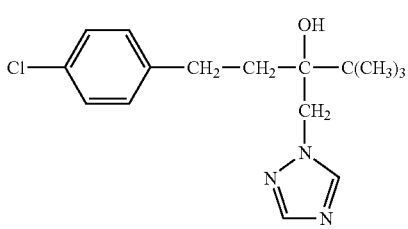

(3-18) ipconazole (known from EP-A 0 329 397) of the formula

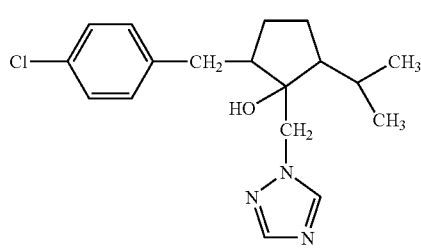

(3-19) metconazole (known from EP-A 0 329 397) of the formula

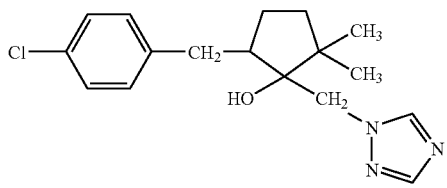

(3-20) triticonazole (known from EP-A 0 378 953) of the formula

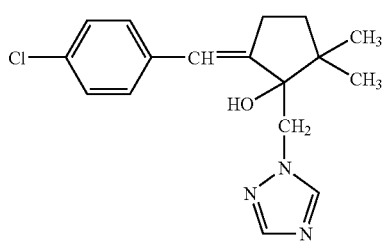

(3-21) bitertanol (known from DE-A 23 24 010) of the formula

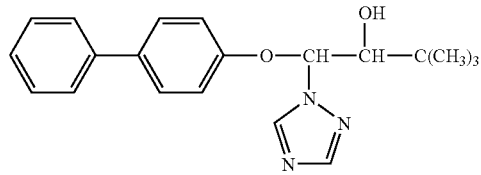

(3-22) triadimenol (known from DE-A 23 24 010) of the formula

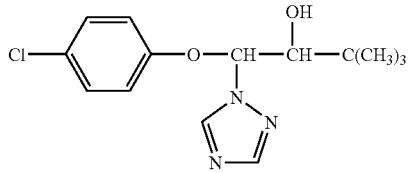

(3-23) triadimefon (known from DE-A 22 01 063) of the formula

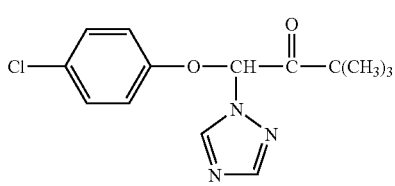

(3-24) fluquinconazole (known from EP-A 0 183 458) of the formula

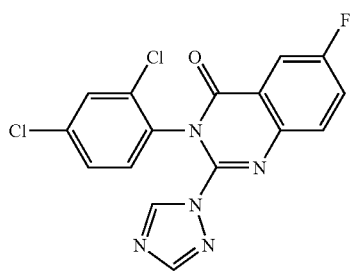

(3-25) quinconazole (known from EP-A 0 183 458) of the formula

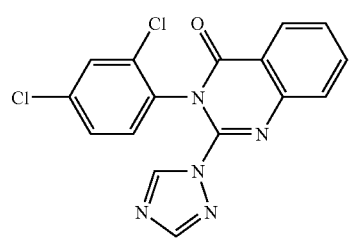

The formula (IV) embraces the following preferred mixing partners of group (4):
(4-1) dichlofluanid (known from DE-A 11 93 498) of the formula

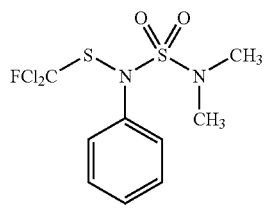

(4-2) tolylfluanid (known from DE-A 11 93 498) of the formula

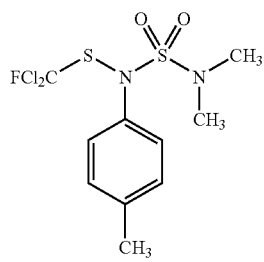

Preferred mixing partners of group (5) are
(5-1) iprovalicarb (known from DE-A 40 26 966) of the formula

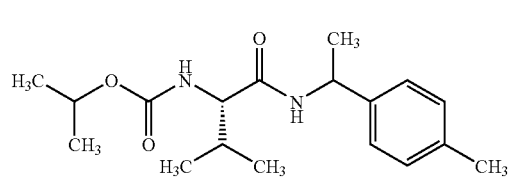

(5-3) benthiavalicarb (known from WO 96/04252) of the formula

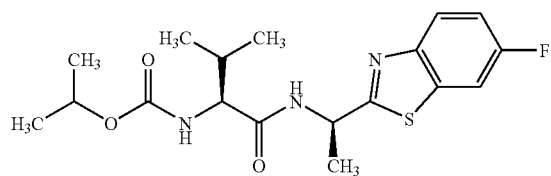

The formula (V) embraces the following preferred mixing partners of group (6):
(6-1) 2-chloro-N-(1,1,3-trimethylindan-4-yl)nicotinamide (known from EP-A 0 256 503) of the formula

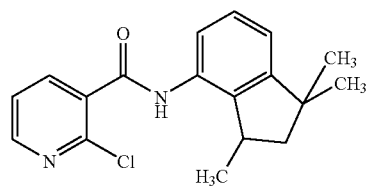

(6-2) boscalid (known from DE-A 195 31 813) of the formula

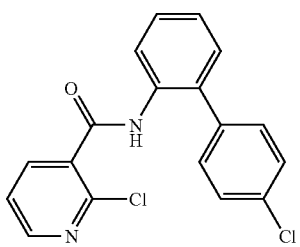

(6-3) furametpyr (known from EP-A 0 315 502) of the formula

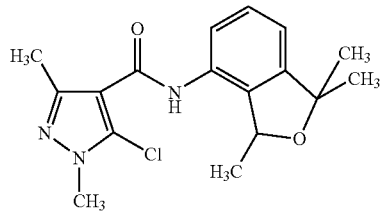

(6-4) N-(3-p-tolylthiophen-2-yl)-1-methyl-3-trifluoromethyl-1H-pyrazole-4-carboxamide (known from EP-A 0 737 682) of the formula

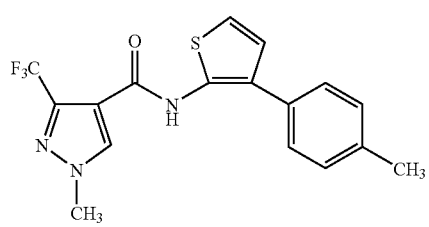

(6-5) ethaboxam (known from EP-A 0 639 574) of the formula

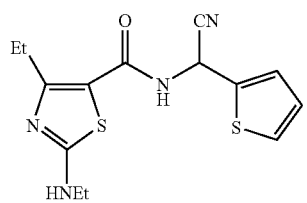

(6-6) fenhexamid (known from EP-A 0 339 418) of the formula

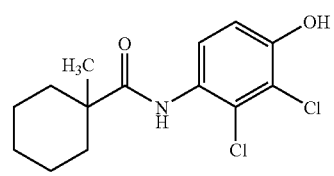

(6-7) carpropamid (known from EP-A 0 341 475) of the formula

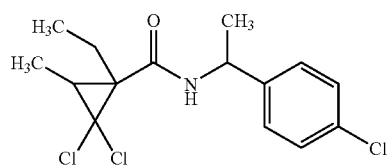

(6-8) 2-chloro-4-(2-fluoro-2-methylpropionylamino)-N,N-dimethylbenzamide (known from EP-A 0 600 629) of the formula

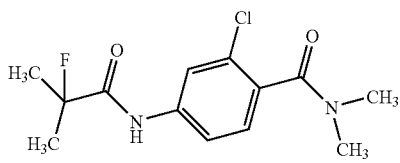

(6-9) fluopicolid (known from WO 99/42447) of the formula

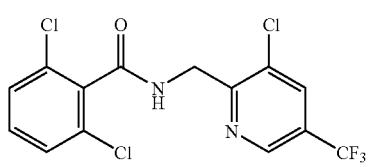

(6-10) zoxamide (known from EP-A 0 604 019) of the formula

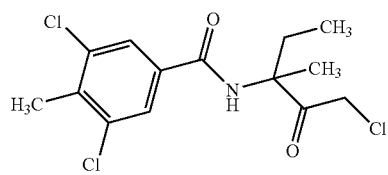

(6-12) carboxin (known from U.S. Pat. No. 3,249,499) of the formula

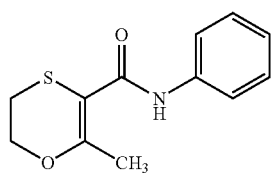

(6-13) tiadinil (known from U.S. Pat. No. 6,616,054) of the formula

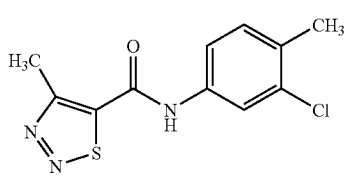

(6-14) penthiopyrad (known from EP-A 0 737 682) of the formula

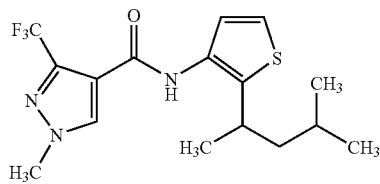

(6-15) silthiofam (known from WO 96/18631) of the formula

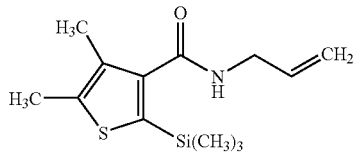

(6-16) N-[2-(1,3-dimethylbutyl)phenyl]-1-methyl-4-(trifluoromethyl)-1H-pyrrole-3-carboxamide (known from WO 02/38542) of the formula

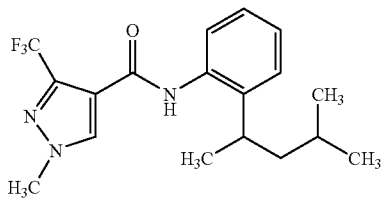

(6-17) flutolanil (known from DE-A 27 31 522) of the formula

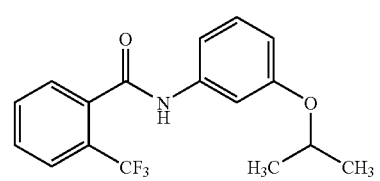

(6-18) N-[2-(1,3-dimethylbutyl)phenyl]-5-fluoro-1,3-dimethyl-1H-pyrazole-4-carboxamide (known from EP-A 1 414 803) of the formula

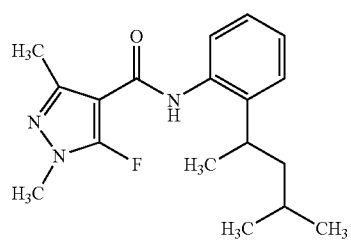

(6-20) N-[2-(1,3-dimethylbutyl)phenyl]-2-(trifluoromethyl)benzamide (known from EP-A 1 519 913) of the formula

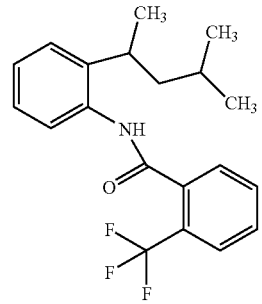

(6-21) N-[2-(1,3-dimethylbutyl)phenyl]-2-iodobenzamide (known from EP-A 1 519 913) of the formula

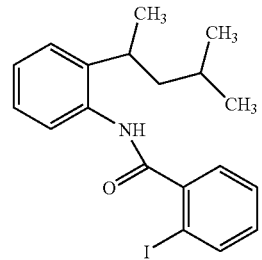

(6-22) N-(4'-chloro-3'-fluorobiphenyl-2-yl)-4-(difluoromethyl)-2-methyl-1,3-thiazole-5-carboxamide (known from EP-A 1 404 407) of the formula

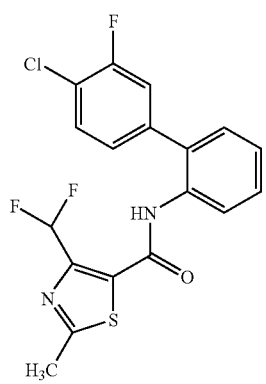

(6-23) N-[5-(4-chlorophenyl)pyrimidin-4-yl]-2-iodo-N-(2-iodobenzoyl)benzamide of the formula

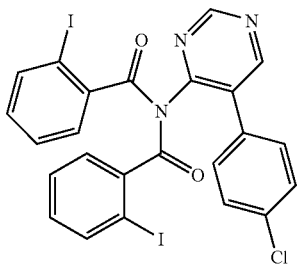

(6-24) N-(3',4'-dichlorobiphenyl-2-yl)-2-methyl-4-(trifluoromethyl)-1,3-thiazole-5-carboxamide (known from EP-A 1 474 406) of the formula

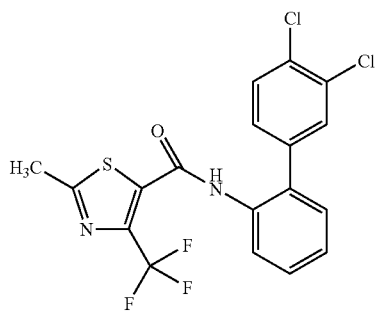

Preferred mixing partners of group (7) are
(7-1) mancozeb (known from DE-A 12 34 704) having the IUPAC name manganese ethylenebis(dithiocarbamate) (polymeric) complex with zinc salt
(7-2) maneb (known from U.S. Pat. No. 2,504,404) of the formula

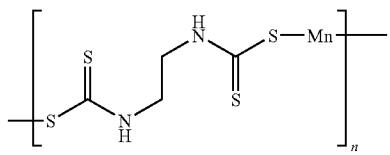

(7-3) metiram (known from DE-A 10 76 434) having the IUPAC name zinc ammoniate ethylenebis(dithiocarbamate)-poly(ethylenethiuram disulphide)
(7-4) propineb (known from GB 935 981) of the formula

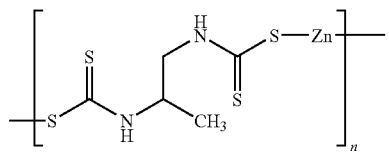

(7-5) thiram (known from U.S. Pat. No. 1,972,961) of the formula

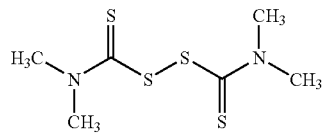

(7-6) zineb (known from DE-A 10 81 446) of the formula

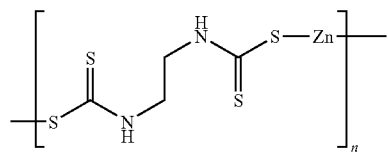

(7-7) ziram (known from U.S. Pat. No. 2,588,428) of the formula

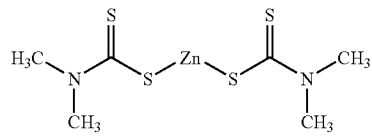

The formula (VI) embraces the following preferred mixing partners of group (8):
(8-1) benalaxyl (known from DE-A 29 03 612) of the formula

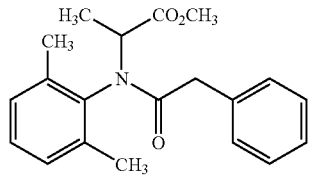

(8-2) furalaxyl (known from DE-A 25 13 732) of the formula

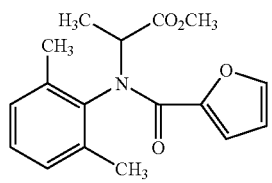

(8-3) metalaxyl (known from DE-A 25 15 091) of the formula

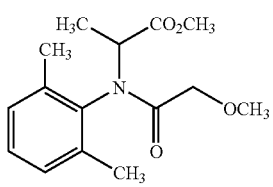

(8-4) metalaxyl-M (known from WO 96/01559) of the formula

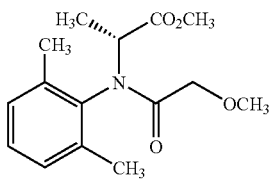

(8-5) benalaxyl-M of the formula

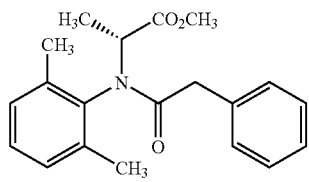

The formula (VII) embraces the following preferred mixing partners of group (9):

(9-1) cyprodinil (known from EP-A 0 310 550) of the formula

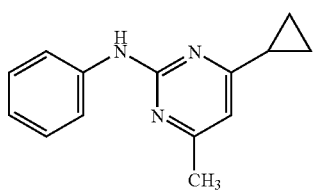

(9-2) mepanipyrim (known from EP-A 0 270 111) of the formula

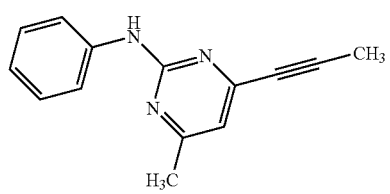

(9-3) pyrimethanil (known from DD 151 404) of the formula

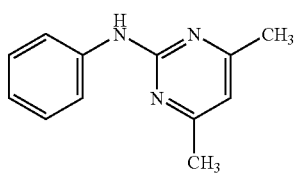

The formula (VIII) embraces the following preferred mixing partners of group (10):

(10-1) 6-chloro-5-[(3,5-dimethylisoxazol-4-yl)sulphonyl]-2,2-difluoro-5H-[1,3]dioxolo[4,5-f]-benzimidazole (known from WO 97/06171) of the formula

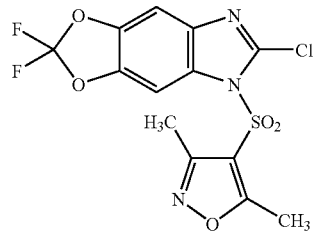

(10-2) benomyl (known from U.S. Pat. No. 3,631,176) of the formula

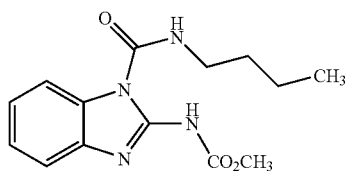

(10-3) carbendazim (known from U.S. Pat. No. 3,010,968) of the formula

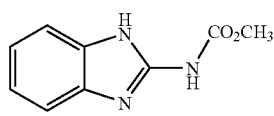

(10-4) chlorfenazole of the formula

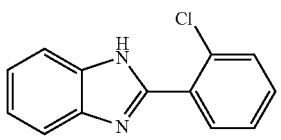

(10-5) fuberidazole (known from DE-A 12 09 799) of the formula

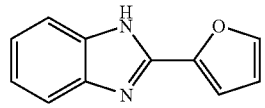

(10-6) thiabendazole (known from U.S. Pat. No. 3,206,468) of the formula

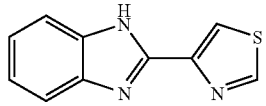

The formula (IX) embraces the following preferred mixing partners of group (11):

(11-1) diethofencarb (known from EP-A 0 078 663) of the formula

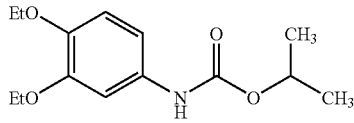

(11-2) propamocarb (known from U.S. Pat. No. 3,513,241) of the formula

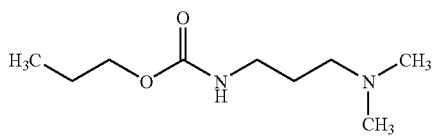

(11-3) propamocarb-hydrochloride (known from U.S. Pat. No. 3,513,241) of the formula

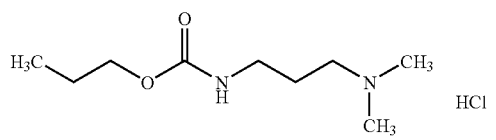

(11-4) propamocarb-fosetyl of the formula

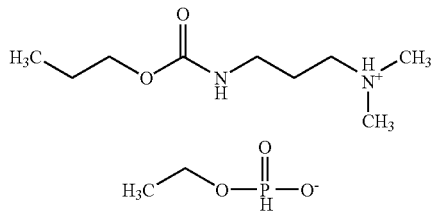

Preferred mixing partners of group (12) are
(12-1) captafol (known from U.S. Pat. No. 3,178,447) of the formula

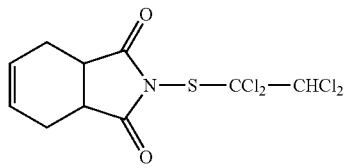

(12-2) captan (known from U.S. Pat. No. 2,553,770) of the formula

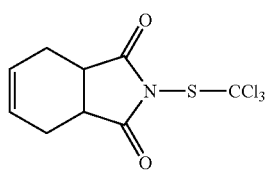

(12-3) folpet (known from U.S. Pat. No. 2,553,770) of the formula

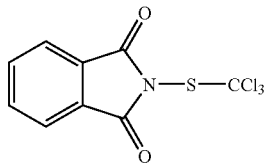

(12-4) iprodione (known from DE-A 21 49 923) of the formula

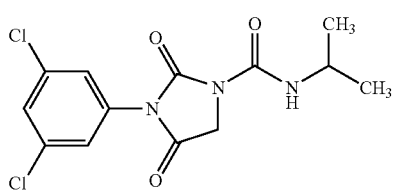

(12-5) procymidone (known from DE-A 20 12 656) of the formula

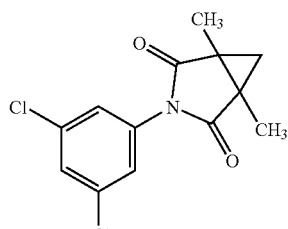

(12-6) vinclozolin (known from DE-A 22 07 576) of the formula

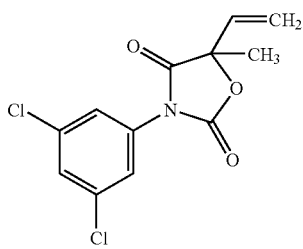

Preferred mixing partners of group (13) are
(13-1) dodine (known from GB 11 03 989) of the formula

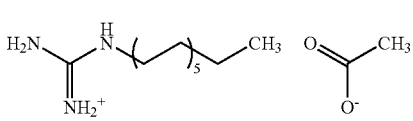

(13-2) guazatine (known from GB 11 14 155)

(13-3) iminoctadine triacetate (known from EP-A 0 155 509) of the formula

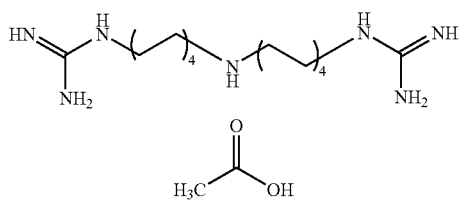

Preferred mixing partners of group (14) are (14-1) cyazofamid (known from EP-A 0 298 196) of the formula

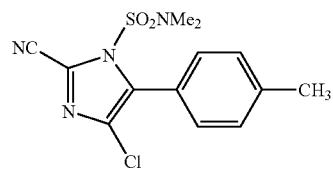

(14-2) prochloraz (known from DE-A 24 29 523) of the formula

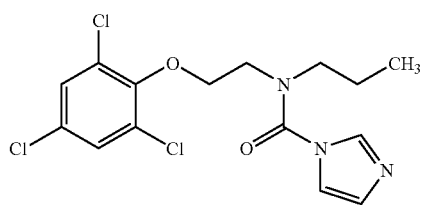

(14-3) triazoxide (known from DE-A 28 02 488) of the formula

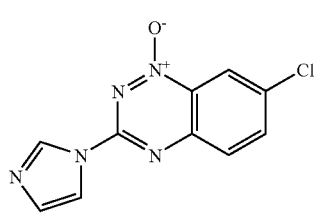

(14-4) pefurazoate (known from EP-A 0 248 086) of the formula

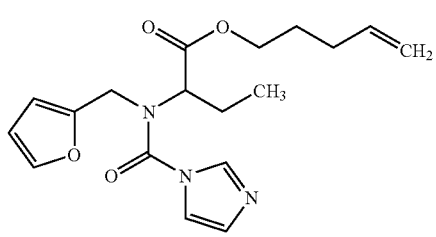

The formula (X) embraces the following preferred mixing partners of group (15):

(15-1) aldimorph (known from DD 140 041) of the formula

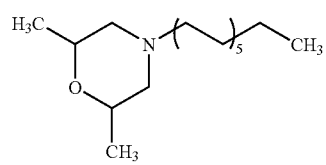

(15-2) tridemorph (known from GB 988 630) of the formula

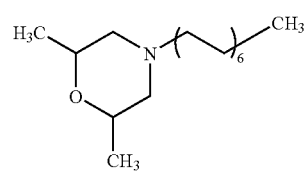

(15-3) dodemorph (known from DE-A 25 432 79) of the formula

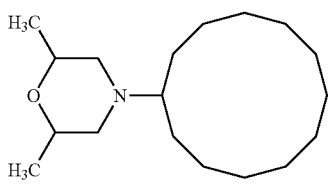

(15-4) fenpropimorph (known from DE-A 26 56 747) of the formula

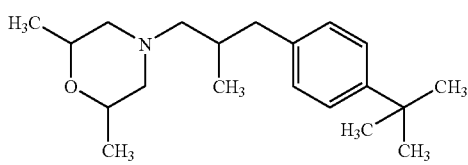

(15-5) dimethomorph (known from EP-A 0 219 756) of the formula

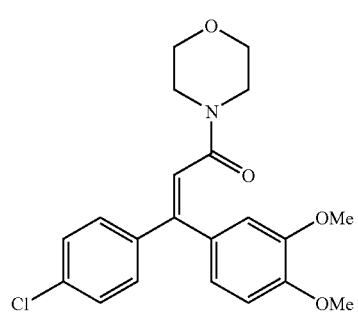

(15-6) flumorph (known from EP-A 0 860 438) of the formula

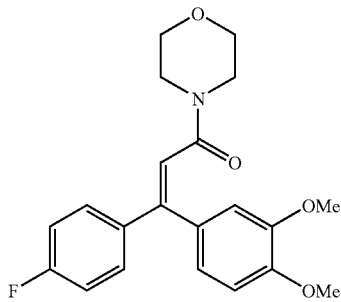

The formula (XI) embraces the following preferred mixing partners of group (16):

(16-1) fenpiclonil (known from EP-A 0 236 272) of the formula

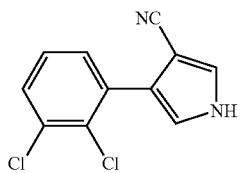

(16-2) fludioxonil (known from EP-A 0 206 999) of the formula

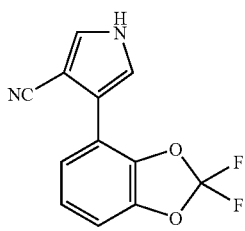

(16-3) pyrrolnitrin (known from JP 65-25876) of the formula

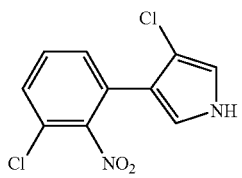

Preferred mixing partners of group (17) are (17-1) fosetyl-Al (known from DE-A 24 56 627) of the formula

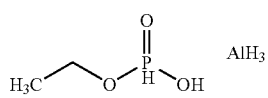

(17-2) phosphonic acid (known chemical) of the formula

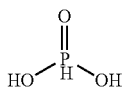

(17-3) tolclofos-methyl (known from DE-A 25 01 040) of the formula

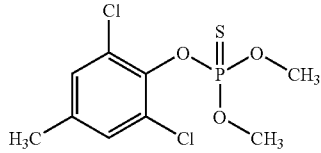

The formula (XII) embraces the following preferred mixing partners of group (18) which are known from WO 96/23793 and can in each case be present as E or Z isomers. Accordingly, compounds of the formula (XII) can be present as a mixture of different isomers or else in the form of a single isomer. Preference is given to compounds of the formula (XII) in the form of their E isomer:

(18-1) the compound 2-(2,3-dihydro-1H-inden-5-yl)-N-[2-(3,4-dimethoxyphenyl)ethyl]-2-(methoxyimino)acetamide of the formula

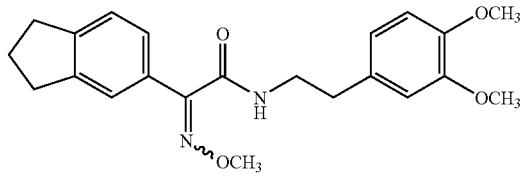

(18-2) the compound N-[2-(3,4-dimethoxyphenyl)ethyl]-2-(methoxyimino)-2-(5,6,7,8-tetrahydro-naphthalen-2-yl)acetamide of the formula

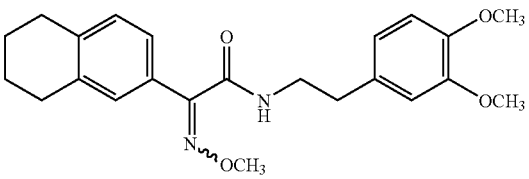

(18-3) the compound 2-(4-chlorophenyl)-N-[2-(3,4-dimethoxyphenyl)ethyl]-2-(methoxyimino)-acetamide of the formula

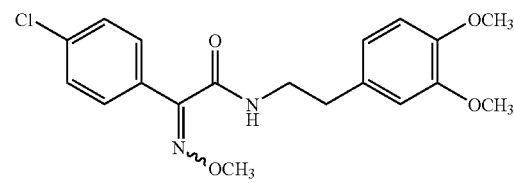

(18-4) the compound 2-(4-bromophenyl)-N-[2-(3,4-dimethoxyphenyl)ethyl]-2-(methoxyimino)-acetamide of the formula

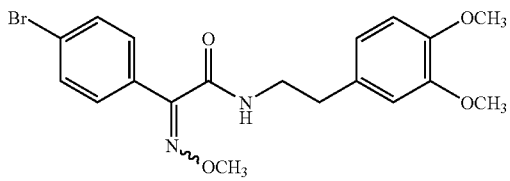

(18-5) the compound 2-(4-methylphenyl)-N-[2-(3,4-dimethoxyphenyl)ethyl]-2-(methoxyimino)-acetamide of the formula

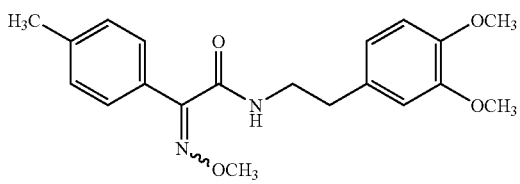

(18-6) the compound 2-(4-ethylphenyl)-N-[2-(3,4-dimethoxyphenyl)ethyl]-2-(methoxyimino)-acetamide of the formula

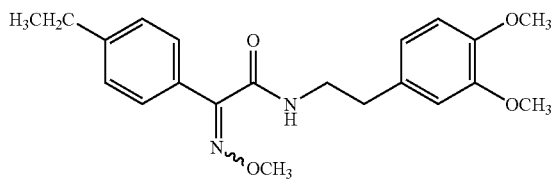

Preferred mixing partners of group (19) are (19-1) acibenzolar-5-methyl (known from EP-A 0 313 512) of the formula

(19-2) chlorothalonil (known from U.S. Pat. No. 3,290,353) of the formula

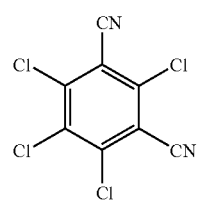

(19-3) cymoxanil (known from DE-A 23 12 956) of the formula

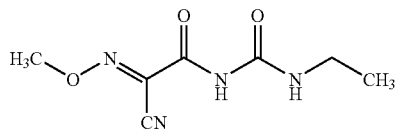

(19-4) edifenphos (known from DE-A 14 93 736) of the formula

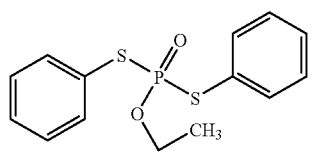

(19-5) famoxadone (known from EP-A 0 393 911) of the formula

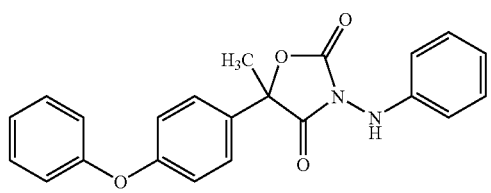

(19-6) fluazinam (known from EP-A 0 031 257) of the formula

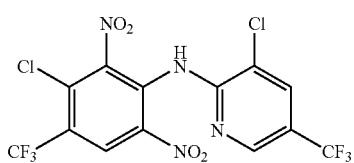

(19-7) copper oxychloride (19-9) oxadixyl (known from DE-A 30 30 026) of the formula

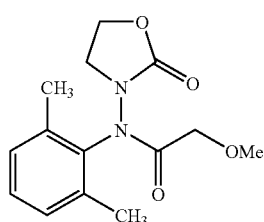

(19-10) spiroxamine (known from DE-A 37 35 555) of the formula

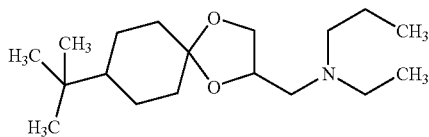

(19-11) dithianon (known from JP-A 44-29464) of the formula

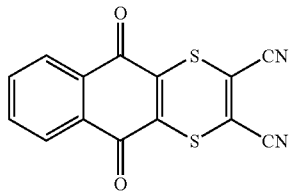

(19-12) metrafenone (known from EP-A 0 897 904) of the formula

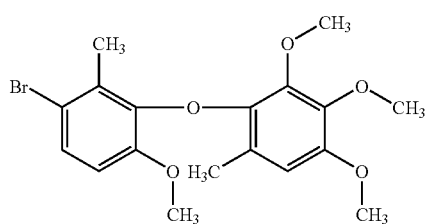

(19-13) 2,3-dibutyl-6-chlorothieno[2,3-d]pyrimidin-4(3H)one (known from WO 99/14202) of the formula

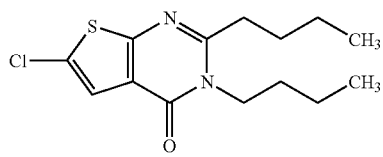

(19-14) probenazole (known from U.S. Pat. No. 3,629,428) of the formula

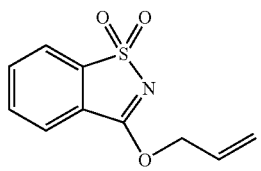

(19-15) isoprothiolane (known from U.S. Pat. No. 3,856,814) of the formula

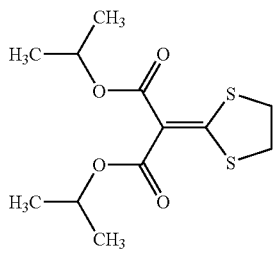

(19-16) kasugamycin (known from GB 1 094 567) of the formula

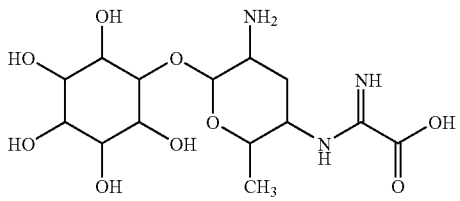

(19-17) phthalide (known from JP-A 57-55844) of the formula

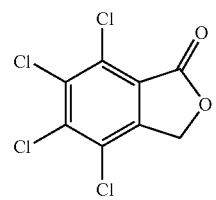

(19-18) ferimzone (known from EP-A 0 019 450) of the formula

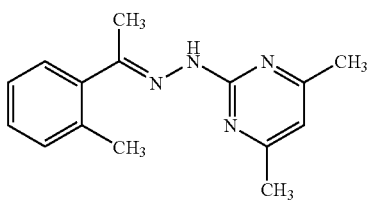

(19-19) tricyclazole (known from DE-A 22 50 077) of the formula

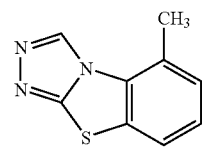

(19-20) cyprosulfamide of the formula

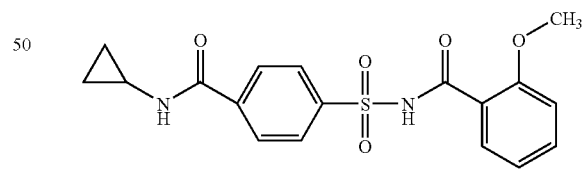

(19-21) mandipropamid (known from WO 01/87822) of the formula

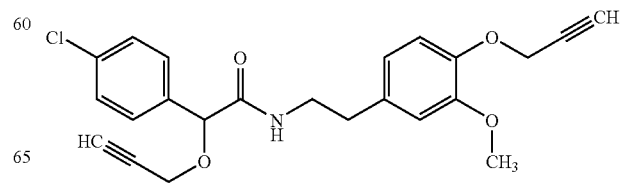

Preferred mixing partners of group (20) are (20-1) pencycuron (known from DE-A 27 32 257) of the formula

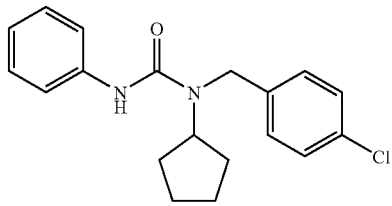

(20-2) thiophanate-methyl (known from DE-A 18 06 123) of the formula

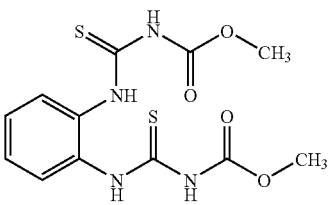

(20-3) thiophanate-ethyl (known from DE-A 18 06 123) of the formula

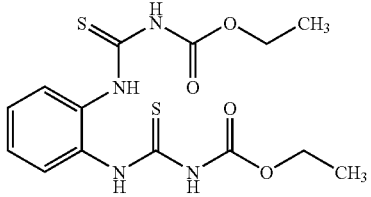

Preferred mixing partners of group (21) are (21-1) fenoxanil (known from EP-A 0 262 393) of the formula

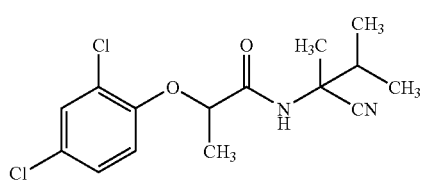

(21-2) diclocymet (known from JP-A 7-206608) of the formula

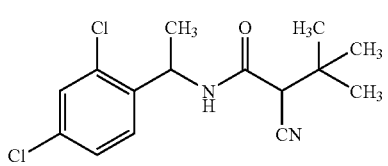

Preferred mixing partners of group (22) are (22-1) 5-chloro-N-[(1S)-2,2,2-trifluoro-1-methylethyl]-6-(2,4,6-trifluorophenyl) [1,2,4]triazolo-[1,5-a]pyrimidine-7-amine (known from U.S. Pat. No. 5,986,135) of the formula

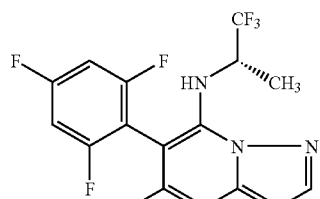

(22-2) 5-chloro-N-[(1R)-1,2-dimethylpropyl]-6-(2,4,6-trifluorophenyl) [1,2,4]triazolo[1,5-a]-pyrimidine-7-amine (known from WO 02/38565) of the formula

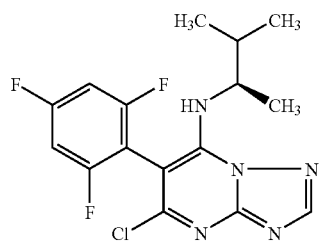

(22-3) 5-chloro-6-(2-chloro-6-fluorophenyl)-7-(4-methylpiperidin-1-yl) [1,2,4]triazolo[1,5-a]-pyrimidine (known from U.S. Pat. No. 5,593,996) of the formula

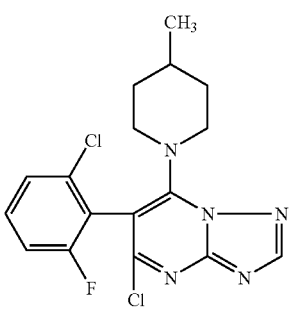

(22-4) 5-chloro-6-(2,4,6-trifluorophenyl)-7-(4-methylpiperidin-1-yl) [1,2,4]triazolo[1,5-a]-pyrimidine (known from DE-A 101 24 208) of the formula

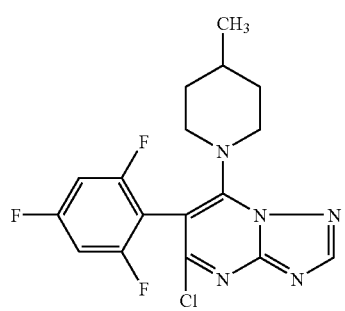

Preferred mixing partners of group (23) are (23-1) 2-butoxy-6-iodo-3-propylbenzopyran-4-one (known from WO 03/014103) of the formula

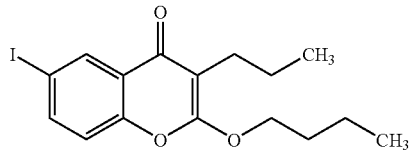

(23-2) 2-ethoxy-6-iodo-3-propylbenzopyran-4-one (known from WO 03/014103) of the formula

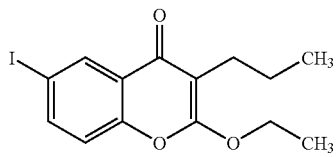

(23-3) 6-iodo-2-propoxy-3-propylbenzopyran-4-one (known from WO 03/014103) of the formula

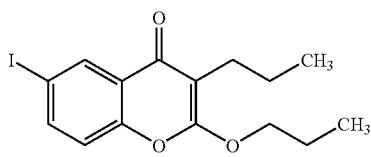

(23-4) 2-but-2-ynyloxy-6-iodo-3-propylbenzopyran-4-one (known from WO 03/014103) of the formula

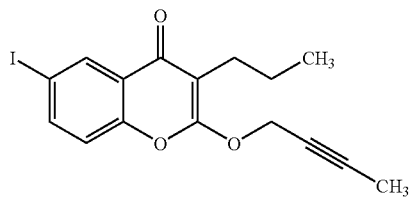

(23-5) 6-iodo-2-(1-methylbutoxy)-3-propylbenzopyran-4-one (known from WO 03/014103) of the formula

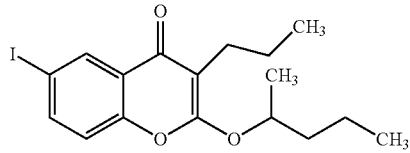

(23-6) 2-but-3-enyloxy-6-iodobenzopyran-4-one (known from WO 03/014103) of the formula

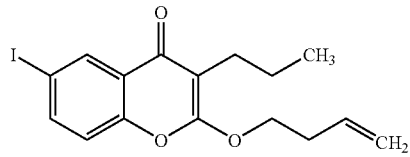

(23-7) 3-butyl-6-iodo-2-isopropoxybenzopyran-4-one (known from WO 03/014103) of the formula

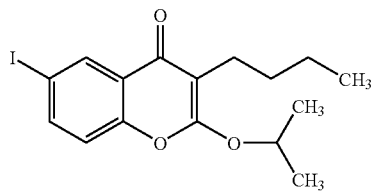

Preferred mixing partners of group (24) are (24-1) N-(3',4'-dichloro-5-fluoro-1,1'-biphenyl-2-yl)-3-(difluoromethyl)-1-methyl-1H-pyrazole-4-carboxamide (known from WO 03/070705) of the formula

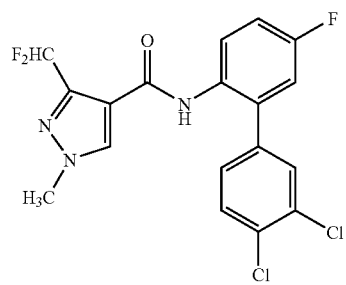

(24-2) 3-(difluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

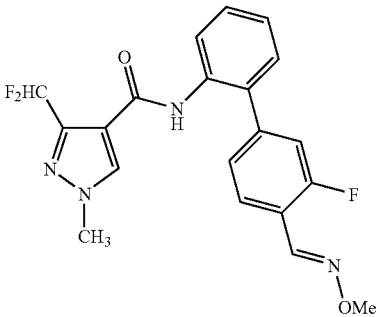

(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

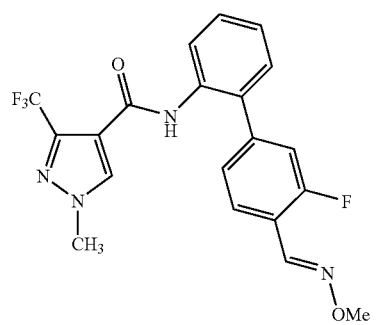

(24-4) N-(3',4'-dichloro-1,1'-biphenyl-2-yl)-5-fluoro-1,3-dimethyl-1H-pyrazole-4-carboxamide (known from WO 00/14701) of the formula

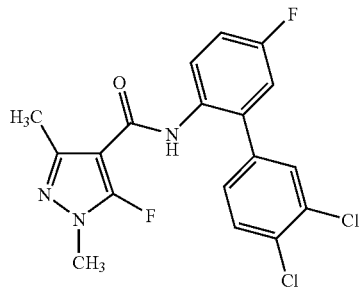

(24-5) N-(4'-chloro-3'-fluoro-1,1'-biphenyl-2-yl)-2-methyl-4-(trifluoromethyl)-1,3-thiazole-5-carboxamide (known from WO 03/066609) of the formula

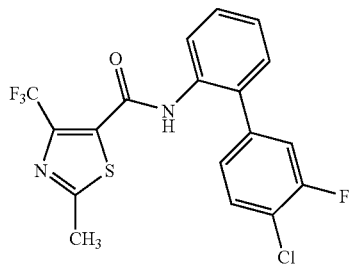

(24-6) N-(4'-chloro-1,1'-biphenyl-2-yl)-4-(difluoromethyl)-2-methyl-1,3-thiazole-5-carboxamide (known from WO 03/066610) of the formula

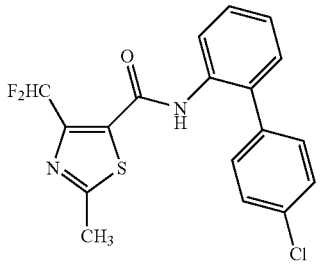

(24-7) N-(4'-bromo-1,1'-biphenyl-2-yl)-4-(difluoromethyl)-2-methyl-1,3-thiazole-5-carboxamide (known from WO 03/066610) of the formula

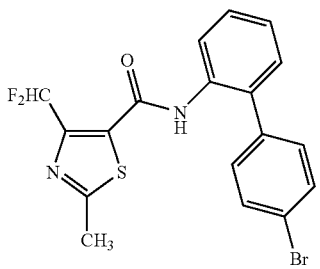

(24-8) 4-(difluoromethyl)-2-methyl-N-[4'-(trifluoromethyl)-1,1'-biphenyl-2-yl]-1,3-thiazole-5-carboxamide (known from WO 03/066610) of the formula

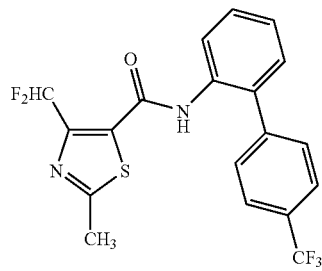

Compound (6-7), carpropamid, has three asymmetrically substituted carbon atoms. Accordingly, compound (6-7) can be present as a mixture of different isomers or else in the form of a single component. Particular preference is given to the compounds (1S,3R)-2,2-dichloro-N-[(1R)-1-(4-chlorophenyl)ethyl]-1-ethyl-3-methylcyclopropanecarboxamide of the Formula

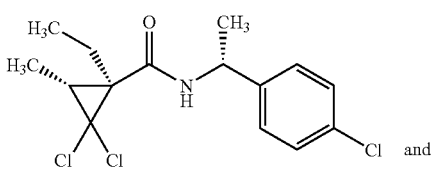 and (1R,3S)-2,2-dichloro-N-[(1R)-1-(4-chlorophenyl)ethyl]-1-ethyl-3-methylcyclopropanecarboxamide of the Formula

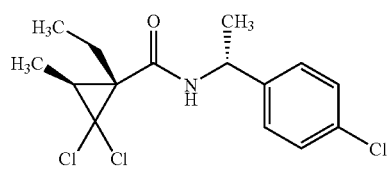

Emphasis is given to active compound combinations comprising the compound of the formula (Ia)

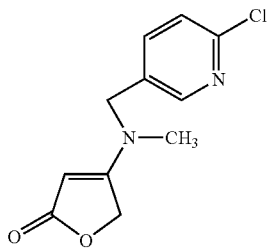

(Ia)

and a compound selected from Groups (2) to (24).

Emphasis is also given to active compound combinations comprising the compound of the formula (Ib)

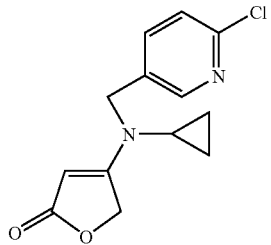

and a compound selected from Groups (2) to (24).

Particularly preferred active compounds of groups (2) to (24) are the following active compounds:
- (2-1) azoxystrobin
- (2-2) fluoxastrobin
- (2-3) (2E)-2-(2-{[6-(3-chloro-2-methylphenoxy)-5-fluoro-4-pyrimidinyl]oxy}phenyl)-2-(methoxyimino)-N-methylethanamide
- (2-4) trifloxystrobin
- (2-5) (2E)-2-(methoxyimino)-N-methyl-2-(2-{[({(1E)-1-[3-(trifluoromethyl)-phenyl]ethylidene}amino)oxy]methyl}phenyl)ethanamide
- (2-6) (2E)-2-(methoxyimino)-N-methyl-2-{2-[(E)-({1-[3-(trifluoromethyl)phenyl]-ethoxy}imino)methyl]phenyl}ethanamide
- (2-8) 5-methoxy-2-methyl-4-(2-{[({(1E)-1-[3-(trifluoromethyl)phenyl]ethylidene}-amino)oxy]methyl}phenyl)-2,4-dihydro-3H-1,2,4-triazol-3-one
- (2-9) kresoxim-methyl
- (2-10) dimoxystrobin
- (2-11) picoxystrobin
- (2-12) pyraclostrobin
- (2-13) metominostrobin
- (3-3) propiconazole
- (3-4) difenoconazole
- (3-6) cyproconazole
- (3-7) hexaconazole
- (3-8) penconazole
- (3-9) myclobutanil
- (3-10) tetraconazole
- (3-12) epoxiconazole
- (3-13) flusilazole
- (3-15) prothioconazole
- (3-16) fenbuconazole
- (3-17) tebuconazole
- (3-18) ipconazole
- (3-19) metconazole
- (3-20) triticonazole
- (3-21) bitertanol
- (3-22) triadimenol
- (3-23) triadimefon
- (3-24) fluquinconazole
- (4-1) dichlofluanid
- (4-2) tolylfluanid
- (5-1) iprovalicarb
- (5-3) benthiavalicarb
- (6-2) boscalid
- (6-5) ethaboxam
- (6-6) fenhexamid
- (6-7) carpropamid
- (6-8) 2-chloro-4-[(2-fluoro-2-methylpropanoyl)amino]-N,N-dimethylbenzamide
- (6-9) fluopicolid
- (6-10) zoxamide
- (6-11) 3,4-dichloro-N-(2-cyanophenyl)isothiazole-5-carboxamide
- (6-14) penthiopyrad
- (6-16) N-[2-(1,3-dimethylbutyl)phenyl]-1-methyl-4-(trifluoromethyl)-1H-pyrrole-3-carboxamide
- (6-17) flutolanil
- (6-18) N-[2-(1,3-dimethylbutyl)phenyl]-5-fluoro-1,3-dimethyl-1H-pyrazole-4-carboxamide
- (7-1) mancozeb
- (7-2) maneb
- (7-4) propineb
- (7-5) thiram
- (7-6) zineb
- (8-1) benalaxyl
- (8-2) furalaxyl
- (8-3) metalaxyl
- (8-4) metalaxyl-M
- (8-5) benalaxyl-M
- (9-1) cyprodinil
- (9-2) mepanipyrim
- (9-3) pyrimethanil
- (10-1) 6-chloro-5-[(3,5-dimethylisoxazol-4-yl)sulphonyl]-2,2-difluoro-5H-[1,3]dioxolo[4,5-f]-benzimidazole
- (10-3) carbendazim
- (11-1) diethofencarb
- (11-2) propamocarb
- (11-3) propamocarb-hydrochloride
- (11-4) propamocarb-fosetyl
- (12-2) captan
- (12-3) folpet
- (12-4) iprodione
- (12-5) procymidone
- (13-1) dodine
- (13-2) guazatine
- (13-3) iminoctadine triacetate
- (14-1) cyazofamid
- (14-2) prochloraz
- (14-3) triazoxide
- (15-4) fenpropimorph
- (15-5) dimethomorph
- (15-6) flumorph
- (16-2) fludioxonil
- (17-1) fosetyl-Al
- (17-2) phosphonic acid
- (17-3) tolclofos-methyl
- (19-1) acibenzolar-5-methyl
- (19-2) chlorothalonil
- (19-3) cymoxanil
- (19-5) famoxadone
- (19-6) fluazinam
- (19-7) copper oxychloride
- (19-9) oxadixyl
- (19-10) spiroxamine
- (19-21) cyprosulfamide
- (19-22) mandipropamid
- (20-1) pencycuron
- (20-2) thiophanate-methyl
- (22-1) 5-chloro-N-[(1S)-2,2,2-trifluoro-1-methylethyl]-6-(2,4,6-trifluorophenyl) [1,2,4]-triazolo[1,5-a]pyrimidine-7-amine
- (22-2) 5-chloro-N-[(1R)-1,2-dimethylpropyl]-6-(2,4,6-trifluorophenyl) [1,2,4]triazolo[1,5-a]-pyrimidine-7-amine (22-4) 5-chloro-6-(2,4,6-trifluorophenyl)-7-(4-methylpiperidin-1-yl)[1,2,4-triazolo[1,5-a]pyrimidine
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one
(24-1) N-(3',4'-dichloro-5-fluoro-1,1'-biphenyl-2-yl)-3-(difluoromethyl)-1-methyl-1H-pyrazole-4-carboxamide
(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide
(24-7) N-(4'-bromo-1,1'-biphenyl-2-yl)-4-(difluoromethyl)-2-methyl-1,3-thiazole-5-carboxamide.

Very particularly preferred active compounds of the groups (2) to (24) are the following active compounds:
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(3-15) prothioconazole
(3-17) tebuconazole
(3-18) ipconazole
(3-20) triticonazole
(3-21) bitertanol
(3-22) triadimenol
(3-24) fluquinconazole
(4-1) dichlofluanid
(4-2) tolylfluanid
(5-1) iprovalicarb
(6-6) fenhexamid
(6-7) carpropamid
(6-9) fluopicolid
(6-14) penthiopyrad
(6-17) flutolanil
(6-18) N-[2-(1,3-dimethylbutyl)phenyl]-5-fluoro-1,3-dimethyl-1H-pyrazole-4-carboxamide
(7-4) propineb
(7-5) thiram
(8-3) metalaxyl
(8-4) metalaxyl-M
(8-5) benalaxyl-M
(9-3) pyrimethanil
(10-3) carbendazim
(11-4) propamocarb-fosetyl
(12-4) iprodione
(14-2) prochloraz
(14-3) triazoxide
(16-2) fludioxonil
(17-3) tolclofos-methyl
(19-10) spiroxamine
(19-21) cyprosulfamide
(19-22) mandipropamid
(20-1) pencycuron
(22-4) 5-chloro-6-(2,4,6-trifluorophenyl)-7-(4-methylpiperidin-1-yl) [1,2,4]triazolo[1,5-a]-pyrimidine
(24-1) N-(3',4'-dichloro-5-fluoro-1,1'-biphenyl-2-yl)-3-(difluoromethyl)-1-methyl-1H-pyrazole-4-carboxamide.

Especially preferred mixing partners are the following active compounds:
(2-2) fluoxastrobin
(2-4) trifloxystrobin
(3-15) prothioconazole
(3-17) tebuconazole
(3-18) ipconazole
(3-20) triticonazole
(3-22) triadimenol
(6-7) carpropamid
(6-18) N-[2-(1,3-dimethylbutyl)phenyl]-5-fluoro-1,3-dimethyl-1H-pyrazole-4-carboxamide
(7-5) thiram
(8-3) metalaxyl
(8-4) metalaxyl-M
(19-21) cyprosulfamide
(20-1) pencycuron
(24-1) N-(3',4'-dichloro-5-fluoro-1,1'-biphenyl-2-yl)-3-(difluoromethyl)-1-methyl-1H-pyrazole-4-carboxamide.

Active compound combinations which are to be emphasized are listed in the table below.

| Active compound of group 1 | Active compound of groups 2 to 24 |
| --- | --- |
| (Ia) | (2-2) fluoxastrobin |
| (Ia) | (2-4) trifloxystrobin |
| (Ia) | (3-15) prothioconazole |
| (Ia) | (3-17) tebuconazole |
| (Ia) | (3-18) ipconazole |
| (Ia) | (3-20) triticonazole |
| (Ia) | (3-22) triadimenol |
| (Ia) | (6-7) carpropamid |
| (Ia) | (6-18) N-[2-(1,3-dimethylbutyl)phenyl]-5-fluoro-1,3-dimethyl-1H-pyrazole-4-carboxamide |
| (Ia) | (7-5) thiram |
| (Ia) | (8-3) metalaxyl |
| (Ia) | (8-4) metalaxyl-M |
| (Ia) | (19-21) cyprosulfamide |
| (Ia) | (20-1) pencycuron |
| (Ia) | (24-1) N-(3',4'-dichloro-5-fluoro-1,1'-biphenyl-2-yl)-3-(difluoromethyl)-1-methyl-1H-pyrazole-4-carboxamide |
| (Ib) | (2-2) fluoxastrobin |
| (Ib) | (2-4) trifloxystrobin |
| (Ib) | (3-15) prothioconazole |
| (Ib) | (3-17) tebuconazole |
| (Ib) | (3-18) ipconazole |
| (Ib) | (3-20) triticonazole |
| (Ib) | (3-22) triadimenol |
| (Ib) | (6-7) carpropamid |
| (Ib) | (6-18) N-[2-(1,3-dimethylbutyl)phenyl]-5-fluoro-1,3-dimethyl-1H-pyrazole-4-carboxamide |
| (Ib) | (7-5) thiram |
| (Ib) | (8-3) metalaxyl |
| (Ib) | (8-4) metalaxyl-M |
| (Ib) | (19-21) cyprosulfamide |
| (Ib) | (20-1) pencycuron |
| (Ib) | (24-1) N-(3',4'-dichloro-5-fluoro-1,1'-biphenyl-2-yl)-3-(difluoromethyl)-1-methyl-1H-pyrazole-4-carboxamide |

Embodiments of the invention which are emphasized for the treatment of seed are mixtures comprising (Ia) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

Embodiments of the invention which are emphasized for the treatment of seed are furthermore mixtures comprising (Ib) and fluoxastrobin (2-2) and/or trifloxystrobin (2-4) and/or prothioconazole (3-15) and/or tebuconazole (3-17) and/or ipconazole (3-18) and/or triticonazole (3-20) and/or triadimenol (3-22) and/or carpropamid (6-7) and/or N-[2-(1,3-dimethylbutyl)phenyl]-5-fluoro-1,3-dimethyl-1H-pyrazole-4-carboxamide (6-18) and/or thiram (7-5) and/or metalaxyl (8-3) and/or metalaxyl-M (8-4) and/or N-({4-[(cyclopropylamino)carbonyl]phenyl}sulphonyl)-2-methoxybenzamide (19-21) and/or pencycuron (20-1) and/or N-(3',4'-dichloro-5-fluoro-1,1'-biphenyl-2-yl)-3-(difluoromethyl)-1-methyl-1H-pyrazole-4-carboxamide (24-1).

In addition to an active compound of the formula (I) from group 1, the active compound combinations according to the invention comprise at least one active compound from the compounds of groups (2) to (24). In addition, they may also comprise further fungicidally active additives.

If the active compounds in the active compound combinations according to the invention are present in certain weight ratios, the synergistic effect is particularly pronounced. However, the weight ratios of the active compounds in the active compound combinations can be varied within a relatively wide range. In general, the active compound combinations according to the invention comprise active compounds of the formula (I) and a mixing partner from one of the groups 2 to 24 in the mixing ratios listed in an exemplary manner in the table below.

The mixing ratios are based on ratios by weight. The ratio is to be understood as active compound of the formula (I): mixing partner

| | Mixing partner | Preferred mixing ratio | Particularly preferred mixing ratio |
|---|---|---|---|
| Group (2): | strobilurins | 125:1 to 1:2000 | 50:1 to 1:1000 |
| Group (3): | triazoles | 125:1 to 1:2000 | 50:1 to 1:1000 |
| Group (4): | sulphenamides | 500:1 to 1:25 | 250:1 to 1:1 |
| Group (5): | valinamides | 125:1 to 1:2000 | 50:1 to 1:1000 |
| Group (6): | carboxamides except for (6-6) | 125:1 to 1:2000 | 50:1 to 1:1000 |
| (6-6) | | 500:1 to 1:25 | 250:1 to 1:1 |
| Group (7): | dithiocarbamates | 500:1 to 1:25 | 250:1 to 1:1 |
| Group (8): | acylalanines | 125:1 to 1:2000 | 50:1 to 1:1000 |
| Group (9): | anilinopyrimidines | 500:1 to 1:25 | 250:1 to 1:1 |
| Group (10): | benzimidazoles | 125:1 to 1:2000 | 50:1 to 1:1000 |
| Group (11): | carbamates | 500:1 to 1:25 | 250:1 to 1:1 |
| Group (12): | dicarboximides | 500:1 to 1:25 | 250:1 to 1:1 |
| Group (13): | guanidines | 125:1 to 1:2000 | 50:1 to 1:1000 |
| Group (14): | imidazoles | 125:1 to 1:2000 | 50:1 to 1:1000 |
| Group (15): | morpholines | 125:1 to 1:2000 | 50:1 to 1:1000 |
| Group (16): | pyrroles | 125:1 to 1:2000 | 50:1 to 1:1000 |
| Group (17): | (thio)phosphonates | 500:1 to 1:25 | 250:1 to 1:1 |
| Group (18): | phenylethanamides | 125:1 to 1:2000 | 50:1 to 1:1000 |
| (19-1): | acibenzolar-S-methyl | 125:1 to 1:2000 | 50:1 to 1:1000 |
| (19-2): | chlorothalonil | 500:1 to 1:25 | 250:1 to 1:1 |
| (19-3): | cymoxanil | 125:1 to 1:2000 | 50:1 to 1:1000 |
| (19-4): | edifenphos | 125:1 to 1:2000 | 50:1 to 1:1000 |
| (19-5): | famoxadone | 125:1 to 1:2000 | 50:1 to 1:1000 |
| (19-6): | fluazinam | 125:1 to 1:2000 | 50:1 to 1:1000 |
| (19-7): | copper oxychloride | 500:1 to 1:25 | 250:1 to 1:1 |
| (19-8): | copper hydroxide | 500:1 to 1:25 | 250:1 to 1:1 |
| (19-9): | oxadixyl | 125:1 to 1:2000 | 50:1 to 1:1000 |
| (19-10): | spiroxamine | 125:1 to 1:2000 | 50:1 to 1:1000 |
| (19-11) | dithianon | 500:1 to 1:25 | 250:1 to 1:1 |
| (19-12) | metrafenone | 125:1 to 1:2000 | 50:1 to 1:1000 |
| (19-14): | 2,3-dibutyl-6-chlorothieno-[2,3-d]pyrimidin-4(3H)one | 125:1 to 1:2000 | 50:1 to 1:1000 |
| (19-15): | probenazole | 125:1 to 1:2000 | 50:1 to 1:1000 |
| (19-16): | isoprothiolane | 125:1 to 1:2000 | 50:1 to 1:1000 |
| (19-17): | kasugamycin | 125:1 to 1:2000 | 50:1 to 1:1000 |
| (19-18): | phthalide | 125:1 to 1:2000 | 50:1 to 1:1000 |
| (19-19): | ferimzone | 125:1 to 1:2000 | 50:1 to 1:1000 |
| (19-20): | tricyclazole | 125:1 to 1:2000 | 50:1 to 1:1000 |
| (19-21): | cyprosulfamide | 125:1 to 1:2000 | 50:1 to 1:1000 |
| (19-22) | 2-(4-chlorophenyl)-N-{2-[3-methoxy-4-(prop-2-yn-1-yloxy)-phenyl]ethyl}-2-prop-2-yn-1-yloxy)acetamide | 125:1 to 1:2000 | 50:1 to 1:1000 |
| Group (20): | (thio)urea derivatives | 125:1 to 1:2000 | 50:1 to 1:1000 |
| Group (21): | amides | 125:1 to 1:2000 | 50:1 to 1:1000 |
| Group (22): | triazolopyrimidines | 125:1 to 1:2000 | 50:1 to 1:1000 |
| Group (23): | iodochromones | 125:1 to 1:2000 | 50:1 to 1:1000 |
| Group (24): | biphenylcarboxamides | 125:1 to 1:2000 | 50:1 to 1:1000 |

In each case, the mixing ratio is to be chosen such that a synergistic mixture is obtained. The mixing ratios between the compound of the formula (I) and a compound of one of the groups (2) to (24) may also vary between the individual compounds of a group.

The active compound combinations according to the invention have very good fungicidal properties and are suitable for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling *Phytophthora infestans, Plasmopara viticola* and *Botrytis cinerea*.

Some pathogens causing fungal and bacterial diseases which come under the generic names listed above may be mentioned by way of example, but not by way of limitation:

The active compound combinations according to the invention have a strong microbicidal action and can be used for controlling unwanted microorganisms, such as fungi and bacteria, in crop protection and in the protection of materials.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Diseases caused by powdery mildew pathogens, such as, for example,

*Blumeria* species, such as, for example, *Blumeria graminis*;
*Podosphaera* species, such as, for example, *Podosphaera leucotricha*;
*Sphaerotheca* species, such as, for example, *Sphaerotheca fuliginea*;
*Uncinula* species, such as, for example, *Uncinula necator*;

Diseases caused by rust disease pathogens, such as, for example,

*Gymnosporangium* species, such as, for example, *Gymnosporangium sabinae*
*Hemileia* species, such as, for example, *Hemileia vastatrix*;
*Phakopsora* species, such as, for example, *Phakopsora pachyrhizi* and *Phakopsora meibomiae*;
*Puccinia* species, such as, for example, *Puccinia recondita*;
*Uromyces* species, such as, for example, *Uromyces appendiculatus*;

Diseases caused by pathogens from the group of the Oomycetes, such as, for example,

*Bremia* species, such as, for example, *Bremia lactucae*;
*Peronospora* species, such as, for example, *Peronospora pisi* or *P. brassicae*;
*Phytophthora* species, such as, for example *Phytophthora infestans*;

*Plasmopara* species, such as, for example, *Plasmopara viticola*;
*Pseudoperonospora* species, such as, for example, *Pseudoperonospora humuli* or *Pseudoperonospora cubensis*;
*Pythium* species, such as, for example, *Pythium ultimum*;
  Leaf blotch diseases and leaf wilt diseases caused, for example, by
*Alternaria* species, such as, for example, *Alternaria solani*;
*Cercospora* species, such as, for example, *Cercospora beticola*;
*Cladiosporium* species, such as, for example, *Cladiosporium cucumerinum*;
*Cochliobolus* species, such as, for example, *Cochliobolus sativus*
(conidia form: *Drechslera*, Syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerelle graminicola*;
*Phaeosphaeria* species, such as, for example, *Phaeosphaeria nodorum*;
*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incamata*;
*Venturia* species, such as, for example, *Venturia inaequalis*;
  Root and stem diseases caused, for example, by
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example *Rhizoctonia solani*;
*Tapesia* species, such as, for example, *Tapesia acuformis*;
*Thielaviopsis* species, such as, for example, *Thielaviopsis basicola*;
  Ear and panicle diseases (including maize cobs) caused, for example, by
*Alternaria* species, such as, for example, *Alternaria* spp.;
*Aspergillus* species, such as, for example, *Aspergillus flavus*;
*Cladosporium* species, such as, for example, *Cladosporium* spp.;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;

Diseases caused by smut fungi, such as, for example,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;
  Fruit rot caused, for example, by
*Aspergillus* species, such as, for example, *Aspergillus flavus*;
*Botrytis* species, such as, for example, *Botrytis cinerea*;
*Penicillium* species, such as, for example, *Penicillium expansum*;
*Sclerotinia* species, such as, for example, *Sclerotinia sclerotiorum*;
*Verticilium* species, such as, for example, *Verticilium alboatrum*;
  Seed- and soil-borne rot and wilt diseases, and also diseases of seedlings, caused, for example, by
*Fusarium* species, such as, for example, *Fusarium culmorum*;
*Phytophthora* species, such as, for example, *Phytophthora cactorum*;
*Pythium* species, such as, for example, *Pythium ultimum*;
*Rhizoctonia* species, such as, for example, *Rhizoctonia solani*;
*Sclerotium* species, such as, for example, *Sclerotium rolfsii*;
  Cancerous diseases, galls and witches' broom caused, for example, by
*Nectria* species, such as, for example, *Nectria galligena*;
  Wilt diseases caused, for example, by
*Monilinia* species, such as, for example, *Monilinia laxa*;
  Deformations of leaves, flowers and fruits caused, for example, by
*Taphrina* species, such as, for example, *Taphrina deformans*;
  Degenerative diseases of woody plants caused, for example, by
*Esca* species, such as, for example, *Phaemoniella clamydospora*;
  Diseases of flowers and seeds caused, for example, by
*Botrytis* species, such as, for example, *Botrytis cinerea*;
  Diseases of plant tubers caused, for example, by
*Rhizoctonia* species, such as, for example, *Rhizoctonia solani*;
  Diseases caused by bacteriopathogens, such as, for example,
*Xanthomonas* species, such as, for example, *Xanthomonas campestris* pv. *oryzae*;
*Pseudomonas* species, such as, for example, *Pseudomonas syringae* pv. *lachrymans*;
*Erwinia* species, such as, for example, *Erwinia amylovora*.
  Preference is given to controlling the following diseases of soya beans:
  fungal diseases on leaves, stems, pods and seeds caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllostica sojaecola*), powdery mildew (*Microsphaera diffusa*), pyrenochaeta leaf spot (*Pyrenochaea glycines*), rhizoctonia aerial, foliage, and web blight (*Rhizoctonia solani*), rust (*Phakopsora pachyrhizi*), scab (*Sphaceloma glycines), stemphylium leaf blight (*Stemphylium botryosum*), target spot (*Corynespora Cassiicola*)

Fungal diseases on roots and the stem base caused, for example, by
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional applications are at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that the particular systemic properties of the compositions according to the invention mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of the seed of cereals (such as wheat, barley, rye and oats), maize and rice is of particular importance.

In the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention are also suitable for increasing the harvest yield. In addition, they show reduced toxicity and are well tolerated by plants.

The active compound combinations according to the invention also have a potent strengthening effect in plants. They are therefore suitable for mobilizing the plants' defences against attack by undesired microorganisms.

Plant-strengthening (resistance-inducing) compounds are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the compounds according to the invention can be employed for protecting plants against attack by the above-mentioned pathogens within a certain period of time after the treatment. The period of time within which their protection is effected generally extends from 1 to 10 days, preferably from 1 to 7 days, after the plants have been treated with the active compounds.

The fact that the active compound combinations, at the concentrations required for the controlling of plant diseases, are well tolerated by plants permits a treatment of above-ground plant parts, of propagation stock and seed, and of the soil.

Here, the active compound combinations according to the invention can be used with particularly good results for controlling cereal diseases, such as, for example, against *Puccinia* species, and diseases in viticulture and in the cultivation of fruit and vegetables, such as, for example, against *Botrytis, Venturia* or *Alternaria* species.

The active compound combinations according to the invention are also suitable for increasing the harvest yield. Moreover, they display a low degree of toxicity and are well tolerated by plants.

If appropriate, the active compound combinations according to the invention can also be used in certain concentrations and application rates as herbicides, for influencing plant growth and for controlling animal pests. If appropriate, they can also be employed as intermediates and precursors for the synthesis of further active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating. Here, the active compound combinations can be prepared prior to the treatment by mixing the individual active compounds. Or the treatment is carried out in succession by initially applying a phthalamide of group (1) followed by treatment with an active compound of groups (2) to (24). However, it is also possible to initially treat the plants or parts of plants with an active compound of groups (2) to (24), followed by treatment with a phthalamide of group (1).

In the protection of materials, the active compound combinations according to the invention can be employed for protecting industrial materials against attack and destruction by undesired microorganisms.

In the present context, industrial materials are understood as meaning non-live materials which have been made for use in technology. For example, industrial materials which are to be protected by active compounds according to the invention from microbial modification or destruction can be glues, sizes, paper and board, textiles, leather, wood, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, wood, paints, cooling lubricants and heat-transfer fluids, particularly preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:
*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

In addition, the active compound combinations according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The active compound combinations can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plants can also be treated.

When employing the active compound combinations according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

According to the invention, the plants listed can be treated particularly advantageously with the active compound mixtures. The preferred ranges indicated above for the active compounds and mixtures also apply to the treatment of these plants. Particular emphasis is given to the treatment of plants with the compounds or mixtures specifically indicated in the present text.

The active compound combinations according to the invention are also suitable for controlling animal pests, preferably arthropods and nematodes, in particular nematodes and insects, which are encountered in agriculture, in animal health, in forestry, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes, vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocelletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

Depending on their particular physical and/or chemical properties, the active compound combinations can be converted into the customary formulations, such as solutions, emulsions, wettable powders, suspensions, powders, foams, dusts, pastes, soluble powders, granules, aerosols, suspoemulsion concentrates, natural and synthetic materials impregnated with active compound, microencapsulations in polymeric substances and in coating materials for seeds, and ULV cool and warm fogging formulations.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic minerals such as finely divided silica, alumina and silicates, suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons such as *Sirex juvencus, Urocerus gigas, Urocerus gigas taignus, Urocerus augur.*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, glues, sizes, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example: construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can equally be employed for protecting objects which come into contact with saltwater or brackish water, such as hulls, screens, nets, buildings, quaysides and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the active compound combinations according to the invention have an outstanding antifouling action.

Use of the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl (2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferable suitable components in combinations with the antifouling compositions according to the invention are:
algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as benzo[b]thiophenecarboxylic acid cyclohexylamide S,S-dioxide, dichlofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole;
molluscicides such as fentin acetate, metaldehyde, methiocarb, niclosamid, thiodicarb and trimethacarb;
or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in seawater. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodnius prolixus, Triatoma infestans*.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed may particularly advantageously, according to the invention, be treated with the active compound mixtures according to the invention. The preference ranges given above for the mixtures also apply to the treatment of these plants. Particular emphasis is given to the treatment of plants with the mixtures listed specifically in the current text.

The good insecticidal and fungicidal action of the active compound combinations according to the invention is demonstrated by the examples below. While the individual active compounds show weaknesses in their action, the combinations show an action which exceeds a simple sum of actions.

A synergistic effect in the insecticides and fungicides is always present when the insecticidal or fungicidal action of the active compound combinations exceeds the total of the action of the active compounds when applied individually.

The expected insecticidal or fungicidal action for a given combination of two active compounds can be calculated as follows, according to S. R. Colby ("Calculating Synergistic and Antagonistic Responses of Herbicide Combinations", Weeds 1967, 15, 20-22):

If

X is the kill rate or efficacy, expressed in % of the untreated control, when employing active compound A at an application rate of m ppm or g/ha, Y is the kill rate or efficacy, expressed in % of the untreated control, when employing active compound B at an application rate of n ppm or g/ha and E is the kill rate or efficacy, expressed in % of the untreated control, when employing active compounds A and B at application rates of m and n ppm or g/ha, then $$E = X + Y - \frac{X \times Y}{100}$$

Here, the kill rate or efficacy is determined in %. 0% means a kill rate or efficacy which corresponds to that of the control, whereas a kill rate of 100% means that all the animals are dead and an efficacy of 100% means that no infection is observed.

If the actual fungicidal or insecticidal action exceeds the calculated value, the action of the combination is superadditive, i.e. a synergistic effect is present. In this case, the actually observed efficacy must exceed the value calculated using the above formula for the expected efficacy (E).

Example A

*Aphis gossypii* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cotton leaves (Gossypium hirsutum) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The kill rates determined are entered into Colby's formula (see page 1).

In this test, for example, the following active compound combinations in accordance with the present application show a synergistically enhanced activity compared to the active compounds applied individually:

TABLE A

Plant-damaging insects
*Aphis gossypii* test

| Active compound | Concentration in ppm | Kill in % after 1$^d$ |
|---|---|---|
| compound (Ib) | 0.8 | 30 |
| metalaxyl | 100 | 10 |

TABLE A-continued

Plant-damaging insects
Aphis gossypii test

| | | found* | calc.** |
|---|---|---|---|
| compound (Ib) + metalaxyl (1:125) according to the invention | 0.8 + 100 | 60 | 37 |

| Active compound | Concentration in ppm | Kill in % after $6^d$ | |
|---|---|---|---|
| compound (Ia) | 0.8 | 70 | |
| | 0.16 | 40 | |
| compound (Ib) | 0.8 | 40 | |
| fludioxonil | 100 | 0 | |

| | | found* | calc.** |
|---|---|---|---|
| compound (Ia) + fludioxonil (1:125) according to the invention | 0.8 + 100 | 95 | 70 |
| trifloxystrobin | 100 | 40 | |

| | | found* | calc.** |
|---|---|---|---|
| compound (Ia) + trifloxystrobin (1:125) according to the invention | 0.8 + 100 | 95 | 82 |
| | 0.16 + 100 | 80 | 64 |

| | | found* | calc.** |
|---|---|---|---|
| compound (Ib) + trifloxystrobin (1:125) according to the invention | 0.8 + 100 | 95 | 64 |

*found = activity found
**calc. = activity calculated using Colby's formula

Example B

*Myzus persicae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the Green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The kill rates determined are entered into Colby's formula (see page 1).

In this test, for example, the following active compound combinations in accordance with the present application show a synergistically enhanced activity compared to the active compounds applied individually:

TABLE B

Plant-damaging insects
*Myzus persicae* test

| Active compound | Concentration in ppm | Kill in % after $1^d$ |
|---|---|---|
| compound (Ia) | 0.8 | 40 |
| | 0.16 | 0 |
| compound (Ib) | 4 | 75 |
| fludioxonil | 100 | 0 |

TABLE B-continued

Plant-damaging insects
*Myzus persicae* test

| | | found* | calc.** |
|---|---|---|---|
| compound (Ia) + fludioxonil (1:625) according to the invention | 0.16 + 100 | 30 | 0 |
| metalaxyl | 100 | | 0 |

| | | found* | calc.** |
|---|---|---|---|
| compound (Ia) + metalaxyl (1:125) according to the invention | 0.8 + 100 | 70 | 40 |
| prothioconazole | 100 | | 0 |

| | | found* | calc.** |
|---|---|---|---|
| compound (Ib) + prothioconazole (1:25) according to the invention | 4 + 100 | 95 | 75 |

| Active compound | Concentration in ppm | Kill in % after $6^d$ | |
|---|---|---|---|
| compound (Ia) | 0.8 | 75 | |
| prothioconazole | 100 | 0 | |

| | | found* | calc.** |
|---|---|---|---|
| compound (Ia) + prothioconazole (1:125) according to the invention | 0.8 + 100 | 98 | 75 |

*found = activity found
**calc. = activity calculated using Colby's formula

Example C

*Phaedon cochleariae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the active compound preparation of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are entered into Colby's formula (see page 1).

In this test, for example, the following active compound combinations in accordance with the present application show a synergistically enhanced activity compared to the active compounds applied individually:

TABLE C

Plant-damaging insects
*Phaedon cochleariae* test

| Active compound | Concentration in ppm | Kill in % after $3^d$ |
|---|---|---|
| compound (Ib) | 200 | 60 |
| propamocarb | 200 | 5 |

TABLE C-continued

Plant-damaging insects

*Phaedon cochleariae* test

|  | found* | calc.** |
|---|---|---|
| compound (Ib) + propamocarb (1:1) according to the invention | 200 + 200 | 80 | 62 |

*found = activity found

**calc. = activity calculated using Colby's formula

The invention claimed is:

1. An active synergistic compound combination comprising
   (a) at least one active compound of formula (I)

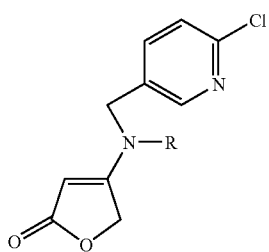

where
   R represents methyl or cyclopropyl, and
   (b) at least one active compound selected from the group consisting of
      Fludioxonil at a weight ratio of the compound of formula (I) to fludioxonil of from 1:50 to 1:625,
      Prothioconazole at a weight ratio of the compound of formula (I) to prothioconazole of from 1:25 to 1:125, and
      Trifloxystrobin at a weight ratio of the compound of formula (I) to trifloxystrobin of from 1:50 to 1:625.

2. The combination according to claim 1, wherein compound (I) is compound (Ia):

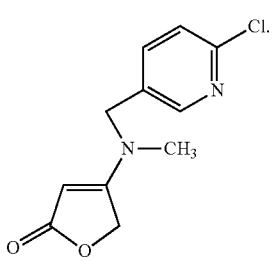

3. The combination according to claim 1, wherein compound (I) is compound (Ib):

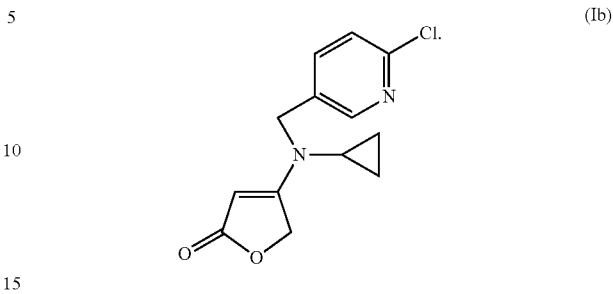

4. A method for treating seed, plant, plant part, and/or soil comprising applying the combination of claim 1 to said seed, plant, plant part, and/or soil.

5. The method of claim 4, wherein the seed, plant, and/or plant part is from a transgenic plant.

6. Seed treated with a composition according to any comprising the combination of claim 1.

7. A method for controlling unwanted animal pests and/or phytopathogenic fungi, said method comprising applying the combination of claim 1 to the unwanted animal pests and/or phytopathogenic fungi and/or their habitat and/or seed.

8. The combination of claim 1, further comprising at least one extender, surfactant, liquid solvent, solid carrier, emulsifier, dispersant, foam former, tackifier, additive, colorant, water repellant, odour-masking agent, anticorrosive agent, binder, resin, fixative, and/or plasticizer.

9. The combination of claim 8, comprising liquid solvent which comprises an organochemical solvent and/or water.

10. The combination of claim 8, that is in the form of a formulation selected from the group consisting of a ready-to-use solution, suspension, wettable powder, paste, soluble powder, dust, granule, emulsion, foam, aerosol, suspoemulsion concentrate, natural and synthetic materials impregnated with active compounds, microencapsulation in polymeric substances, ULV cool formulation, and warm fogging formulation.

11. The formulation of claim 10, comprising between 0.1% to 95% by weight of the active compounds.

12. The method of claim 4, wherein the combination of claim 1 is applied to the seed before, during, and/or after storage;
   applied to the seed before introduction into the soil; and/or
   applied to the seed before, during, and/or after germination.

13. The method of claim 4, wherein the combination is applied to seed of wheat, barley, rye, millet, oats, maize, cotton, soya beans, rice, potatoes, oilseed rape, sunflowers, beans, coffee, beet, peanut, vegetable, fruit, lawn, and/or an ornamental plant.

14. The method of claim 13, wherein the vegetable is cabbage, tomato, cucumber, onion, or lettuce, and wherein the fruit is apple, pear, citrus fruit, or grapes.

15. The method of claim 4, wherein the active compounds are applied simultaneously or applied sequentially.

16. The method of claim 4, wherein the combination is applied to the plant or plant part at an application rate between 0.1 and 10,000 g/ha; applied to the seed at an application rate between 0.01 and 10 g per kg of seed; and/or applied to the soil at an application rate between 0.1 and 10,000 g/ha.

17. The method of claim 7 for controlling fungi, wherein the fungi is are Plasmodiophoromycetes, Oomycetes, Chytridionycetes, Zygomycetes, Ascomycetes, Basidiomycetes, Deuteromycetes, *Phytophthora infestans, Plasmo-*

*para viticola, Botrytis* species, *Puccinia* species, *Venturia* species, and/or *Alternaria* species.

18. The method of claim 7 for controlling pests, wherein the pest is *Aphis gossypii, Myzus persicae*, and/or *Phaedon cochleariae*.

19. An active synergistic compound combination according to claim 1 comprising (a) at least one active compound of formula (I)

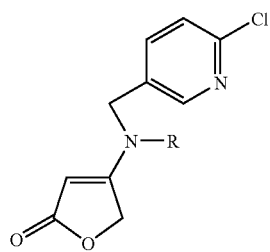

where

R represents methyl or cyclopropyl, and (b) Fludioxonil at a weight ratio of the compound of formula (I) to fludioxonil of from 1:50 to 1:625.

20. An active synergistic compound combination according to claim 19 wherein the weight ratio of the compound of formula (I) to fludioxonil is from 1:125 to 1:625.

21. An active synergistic compound combination according to claim 1 comprising (a) at least one active compound of formula (I)

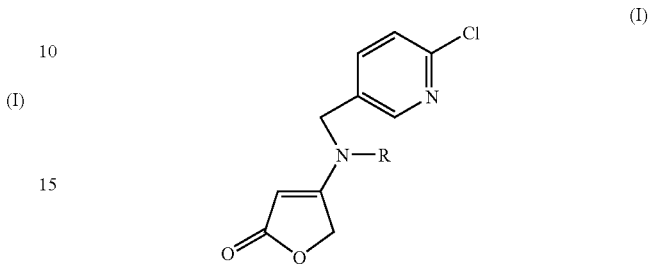

where

R represents methyl or cyclopropyl, and (b) Trifloxystrobin at a weight ratio of the compound of formula (I) to trifloxystrobin of from 1:50 to 1:625.

22. An active synergistic compound combination according to claim 21 wherein the weight ratio of the compound of formula (I) to trifloxystrobin is from 1:125 to 1:625.

* * * * *